US011738214B2

(12) United States Patent
Carpentier et al.

(10) Patent No.: US 11,738,214 B2
(45) Date of Patent: Aug. 29, 2023

(54) IMPLANTABLE ULTRASOUND GENERATING TREATING DEVICE FOR BRAIN TREATMENT, APPARATUS COMPRISING SUCH DEVICE AND METHOD IMPLEMENTING SUCH DEVICE

(71) Applicants: SORBONNE UNIVERSITE, Paris (FR); ASSISTANCE PUBLIQUE—HOPITAUX DE PARIS, Paris (FR); CARTHERA, Paris (FR)

(72) Inventors: Alexandre Carpentier, Paris (FR); Michael Canney, Denver, CO (US); Matthieu Cholvy, Peage de Roussillon (FR)

(73) Assignees: SORBONNE UNIVERSITE, Paris (FR); ASSISTANCE PUBLIQUE—HÔPITAUX DE PARIS, Paris (FR); CARTHERA, Paris (FR)

( * ) Notice: Subject to any disclaimer, the term of this patent is extended or adjusted under 35 U.S.C. 154(b) by 139 days.

(21) Appl. No.: 16/853,637

(22) Filed: Apr. 20, 2020

(65) Prior Publication Data
US 2020/0254284 A1 Aug. 13, 2020

Related U.S. Application Data

(62) Division of application No. 15/536,996, filed as application No. PCT/IB2015/002508 on Dec. 18, 2015, now abandoned.

(30) Foreign Application Priority Data

Dec. 19, 2014 (WO) .................. PCT/IB2014/003102

(51) Int. Cl.
A61N 7/00 (2006.01)
A61M 37/00 (2006.01)
(Continued)

(52) U.S. Cl.
CPC ............ *A61N 7/00* (2013.01); *A61M 37/0092* (2013.01); *A61B 2090/378* (2016.02); *A61N 7/02* (2013.01);
(Continued)

(58) Field of Classification Search
CPC .... A61N 7/00; A61N 7/02; A61N 2007/0021; A61N 2007/0026; A61N 2007/0043;
(Continued)

(56) References Cited

U.S. PATENT DOCUMENTS 1,879,502 A 9/1932 Rinman
4,605,009 A * 8/1986 Pourcelot ............. A61B 8/4488
600/463
(Continued)

FOREIGN PATENT DOCUMENTS

CN 101152646 4/2008
CN 102 670 264 9/2012
(Continued)

*Primary Examiner* — Hien N Nguyen
(74) *Attorney, Agent, or Firm* — Clark & Brody LP

(57) ABSTRACT

An apparatus having an implantable ultrasound generating treating device to induce brain disorder treatment, suitable for implantation in or under the skull bone of a patient, includes several ultrasound generating transducers, which are connectable by a common electrical connection circuit to a generator, and wherein the ultrasound generating transducers each have one or several operating frequencies. The transducers include the group of transducers having several transducers driven by a same electrical drive signal, and connected to the generator system by a common electrical connection circuit, where the electric drive signal serves (Continued)

both as power signal and as a control signal for operating selectively, within said group, at least one or the other of a first transducer or sub-group of transducers, and of a second transducer or sub-group of transducers. The apparatus is also used to treat brain disorders.

21 Claims, 10 Drawing Sheets

(51) Int. Cl.
    *A61B 90/00*     (2016.01)
    *A61N 7/02*     (2006.01)

(52) U.S. Cl.
    CPC ............... *A61N 2007/0021* (2013.01); *A61N 2007/0026* (2013.01); *A61N 2007/0043* (2013.01); *A61N 2007/0047* (2013.01); *A61N 2007/0073* (2013.01); *A61N 2007/0078* (2013.01)

(58) Field of Classification Search
    CPC .... A61N 2007/0047; A61N 2007/0073; A61N 2007/0078; A61M 37/0092; A61B 2090/378
    See application file for complete search history.

(56) References Cited

U.S. PATENT DOCUMENTS

| | | | |
|---|---|---|---|
| 4,646,756 A | 3/1987 | Watmough et al. | |
| 4,836,191 A | 6/1989 | Noske et al. | |
| 5,321,104 A | 6/1994 | Sumino et al. | |
| 5,501,655 A | 3/1996 | Rolt et al. | |
| 5,524,624 A | 6/1996 | Tepper et al. | |
| 5,752,515 A | 5/1998 | Jolesz et al. | |
| 6,139,241 A | 10/2000 | Craig et al. | |
| 6,254,553 B1 | 7/2001 | Lidgren et al. | |
| 6,254,624 B1 | 7/2001 | Oddsen | |
| 6,319,241 B1 | 11/2001 | King et al. | |
| 6,468,219 B1 | 10/2002 | Njemanze | |
| 6,560,486 B1 | 5/2003 | Osorio et al. | |
| 6,585,763 B1 * | 7/2003 | Keilman ................. A61B 8/06 623/1.42 | |
| 6,613,005 B1 | 9/2003 | Friedman et al. | |
| 6,666,833 B1 | 12/2003 | Friedman et al. | |
| 6,862,479 B1 | 3/2005 | Whitehurst et al. | |
| 7,101,337 B2 | 9/2006 | Aubry et al. | |
| 7,107,104 B2 | 9/2006 | Keravel et al. | |
| 7,211,060 B1 | 5/2007 | Talish et al. | |
| 7,522,962 B1 | 4/2009 | Doron et al. | |
| 7,575,550 B1 | 8/2009 | Govari | |
| 7,878,977 B2 | 2/2011 | Mo et al. | |
| 7,896,821 B1 | 3/2011 | Magnin et al. | |
| 8,301,262 B2 * | 10/2012 | Mi ...................... A61B 5/0031 607/30 | |
| 8,977,361 B2 | 3/2015 | Carpentier et al. | |
| 9,993,337 B1 | 6/2018 | Brogan | |
| 2001/0051819 A1 | 12/2001 | Fischell et al. | |
| 2002/0002371 A1 | 1/2002 | Acker et al. | |
| 2002/0038086 A1 | 3/2002 | Hynynen et al. | |
| 2002/0072741 A1 | 6/2002 | Sliwa et al. | |
| 2002/0177792 A1 | 11/2002 | Ooba et al. | |
| 2003/0092987 A1 | 5/2003 | Hynynen et al. | |
| 2003/0135135 A1 | 7/2003 | Miwa et al. | |
| 2003/0195584 A1 | 10/2003 | Dawson | |
| 2003/0225331 A1 | 12/2003 | Diederich et al. | |
| 2004/0049134 A1 | 3/2004 | Tosoya et al. | |
| 2004/0054282 A1 | 3/2004 | Aubry et al. | |
| 2004/0116772 A1 | 6/2004 | Lupin et al. | |
| 2004/0122323 A1 | 6/2004 | Vortman et al. | |
| 2004/0162507 A1 | 8/2004 | Govari | |
| 2004/0236253 A1 | 11/2004 | Vortman et al. | |
| 2004/0267234 A1 * | 12/2004 | Heart ................. A61M 31/002 604/500 | |
| 2005/0020945 A1 | 1/2005 | Tosoya et al. | |
| 2005/0021117 A1 | 1/2005 | He et al. | |
| 2005/0283203 A1 | 12/2005 | Flaherty et al. | |
| 2006/0049957 A1 | 3/2006 | Surgenor et al. | |
| 2006/0079816 A1 | 4/2006 | Barthe et al. | |
| 2006/0129204 A1 | 6/2006 | Pless et al. | |
| 2006/0224060 A1 | 10/2006 | Garell et al. | |
| 2006/0241529 A1 | 10/2006 | Hynynen et al. | |
| 2007/0016041 A1 | 1/2007 | Nita | |
| 2007/0038100 A1 | 2/2007 | Nita | |
| 2007/0067003 A1 | 3/2007 | Sanchez et al. | |
| 2007/0073135 A1 | 3/2007 | Lee et al. | |
| 2007/0179558 A1 | 8/2007 | Gliner et al. | |
| 2007/0219547 A1 | 9/2007 | Osypka | |
| 2007/0225773 A1 | 9/2007 | Shen et al. | |
| 2007/0293908 A1 | 12/2007 | Cowan et al. | |
| 2008/0004676 A1 | 1/2008 | Osypka et al. | |
| 2008/0140149 A1 | 6/2008 | John et al. | |
| 2008/0183166 A1 | 7/2008 | Miller | |
| 2008/0195160 A1 | 8/2008 | Wingeier et al. | |
| 2008/0221490 A1 | 9/2008 | Zahos | |
| 2008/0249409 A1 | 10/2008 | Fraser et al. | |
| 2008/0275526 A1 | 11/2008 | Lozano | |
| 2008/0319355 A1 | 12/2008 | Nita | |
| 2008/0319375 A1 | 12/2008 | Hardy | |
| 2009/0005711 A1 | 1/2009 | Konofagou et al. | |
| 2009/0082860 A1 | 3/2009 | Schieber | |
| 2009/0093724 A1 | 4/2009 | Pernot et al. | |
| 2009/0112278 A1 | 4/2009 | Wingeier et al. | |
| 2009/0112280 A1 | 4/2009 | Wingeier et al. | |
| 2009/0149781 A1 | 6/2009 | Liu et al. | |
| 2009/0238763 A1 | 9/2009 | Yu et al. | |
| 2009/0248165 A1 | 10/2009 | Lin et al. | |
| 2009/0254134 A1 | 10/2009 | Nikolov et al. | |
| 2010/0010394 A1 | 1/2010 | Liu et al. | |
| 2010/0030076 A1 * | 2/2010 | Vortman ............... G01S 7/5209 601/2 | |
| 2010/0041988 A1 | 2/2010 | Pijnenburg et al. | |
| 2010/0056924 A1 | 3/2010 | Powers | |
| 2010/0137937 A1 | 6/2010 | John et al. | |
| 2010/0143241 A1 | 6/2010 | Johnson et al. | |
| 2010/0145414 A1 | 6/2010 | Decre et al. | |
| 2010/0160779 A1 | 6/2010 | Browning et al. | |
| 2010/0217160 A1 | 8/2010 | Saguchi et al. | |
| 2010/0222715 A1 | 9/2010 | Nita | |
| 2010/0224950 A1 | 9/2010 | Dinyari | |
| 2010/0249597 A1 | 9/2010 | Shi | |
| 2010/0268088 A1 | 10/2010 | Prus et al. | |
| 2011/0040172 A1 | 2/2011 | Carpentier et al. | |
| 2011/0046694 A1 | 2/2011 | Forsell | |
| 2011/0051554 A1 | 3/2011 | Varray et al. | |
| 2011/0089160 A1 | 4/2011 | Kuriki | |
| 2011/0112394 A1 | 5/2011 | Mishelevich | |
| 2011/0178441 A1 | 7/2011 | Tyler | |
| 2011/0178442 A1 | 7/2011 | Mishelevich | |
| 2011/0208095 A1 | 8/2011 | Jolesz et al. | |
| 2011/0213200 A1 | 9/2011 | Mishelevich | |
| 2011/0245734 A1 | 10/2011 | Wagner et al. | |
| 2011/0270136 A1 * | 11/2011 | Vitek ..................... A61N 7/02 601/2 | |
| 2011/0295105 A1 | 12/2011 | Konofagou et al. | |
| 2012/0010711 A1 | 1/2012 | Antonyshyn | |
| 2012/0046531 A1 | 2/2012 | Hua | |
| 2012/0065458 A1 | 3/2012 | Tol | |
| 2012/0078140 A1 | 3/2012 | Nita | |
| 2012/0083719 A1 | 4/2012 | Mishelevich | |
| 2012/0109019 A1 | 5/2012 | Schneider et al. | |
| 2012/0123270 A1 | 5/2012 | Klee et al. | |
| 2012/0130288 A1 | 5/2012 | Holland et al. | |
| 2012/0143058 A1 | 6/2012 | Powers et al. | |
| 2012/0172949 A1 | 7/2012 | Wagenaar Cacciola et al. | |
| 2012/0203079 A1 | 8/2012 | McLaughlin | |
| 2012/0277639 A1 | 11/2012 | Pollock et al. | |
| 2012/0283502 A1 | 11/2012 | Mishelevich et al. | |
| 2012/0323147 A1 | 12/2012 | Scheirer et al. | |
| 2013/0006106 A1 | 1/2013 | O'Reilly et al. | |
| 2013/0046229 A1 | 2/2013 | Konofagou et al. | |
| 2013/0049534 A1 | 2/2013 | Clark et al. | |
| 2013/0079682 A1 | 3/2013 | Mishelevich | |

(56) References Cited

U.S. PATENT DOCUMENTS

| | | | |
|---|---|---|---|
| 2013/0131754 A1 | 5/2013 | Sarvazyan | |
| 2013/0178764 A1 | 7/2013 | Eckhouse et al. | |
| 2013/0178765 A1 | 7/2013 | Mishelevich | |
| 2013/0204316 A1 | 8/2013 | Carpentier et al. | |
| 2013/0251633 A1 | 9/2013 | Borden et al. | |
| 2013/0281890 A1 | 10/2013 | Mishelevich | |
| 2013/0303917 A1 | 11/2013 | Ona et al. | |
| 2013/0324891 A1 | 12/2013 | Towe | |
| 2013/0324892 A1 | 12/2013 | Zhu et al. | |
| 2013/0331685 A1 | 12/2013 | Liu et al. | |
| 2013/0338526 A1 | 12/2013 | Howard | |
| 2014/0005521 A1 | 1/2014 | Kohler et al. | |
| 2014/0058293 A1 | 2/2014 | Hynynen et al. | |
| 2014/0074076 A1 | 3/2014 | Gertner | |
| 2014/0114216 A1 | 4/2014 | Konofagou et al. | |
| 2014/0249454 A1 | 9/2014 | Carpentier | |
| 2014/0296646 A1 | 10/2014 | Wingeier et al. | |
| 2014/0330123 A1 | 11/2014 | Manwaring et al. | |
| 2015/0005614 A1 | 1/2015 | Heggeness et al. | |
| 2015/0005860 A1 | 1/2015 | Howard et al. | |
| 2015/0045724 A1 | 2/2015 | Chen et al. | |
| 2015/0065871 A1 | 3/2015 | Konofagou et al. | |
| 2015/0133785 A1 | 5/2015 | Schlenger | |
| 2015/0148710 A1 | 5/2015 | Towe et al. | |
| 2015/0224345 A1 | 8/2015 | Warlick | |
| 2015/0265305 A1 | 9/2015 | Stulen et al. | |
| 2015/0297176 A1 | 10/2015 | Rincker et al. | |
| 2016/0000411 A1 | 1/2016 | Raju et al. | |
| 2016/0001096 A1 | 1/2016 | Mishelevich | |
| 2016/0016012 A1 | 1/2016 | Youn et al. | |
| 2016/0107002 A1 | 4/2016 | Nita | |
| 2016/0151618 A1 | 6/2016 | Powers et al. | |
| 2016/0184614 A1 | 6/2016 | Matula et al. | |
| 2016/0242648 A1 | 8/2016 | Konofagou et al. | |
| 2016/0338663 A1 | 11/2016 | Chen et al. | |
| 2018/0263602 A1 | 9/2018 | Elvira Seguro et al. | |
| 2018/0353777 A1 | 12/2018 | Dianis et al. | |
| 2021/0106849 A1 | 4/2021 | Liu et al. | |

FOREIGN PATENT DOCUMENTS

| | | |
|---|---|---|
| CN | 103 142 287 | 6/2013 |
| DE | 3150513 | 6/1983 |
| DE | 19 641 935 | 9/1997 |
| DE | 10 2010 001020 | 7/2011 |
| EP | 0 643 982 | 3/1995 |
| EP | 0 701 840 | 3/1996 |
| EP | 1 262 160 | 12/2002 |
| EP | 1 312 423 | 5/2003 |
| EP | 1 774 989 | 4/2007 |
| EP | 1 806 238 | 7/2007 |
| EP | 1 834 646 | 9/2007 |
| GB | 2 445 585 | 7/2008 |
| GB | 2 473 265 | 3/2011 |
| JP | 60-75809 | 4/1985 |
| JP | 05-68684 | 3/1993 |
| JP | 2001-327495 | 11/2001 |
| JP | 2003-325616 | 11/2003 |
| JP | 2007-289715 | 11/2007 |
| WO | 92/12605 | 7/1992 |
| WO | 92/22350 | 12/1992 |
| WO | 96/39079 | 12/1996 |
| WO | 98/47569 | 10/1998 |
| WO | 99/34758 | 7/1999 |
| WO | 00/78232 | 12/2000 |
| WO | 01/09111 | 2/2001 |
| WO | 02/100480 | 12/2002 |
| WO | 03/059437 | 7/2003 |
| WO | 03/061756 | 7/2003 |
| WO | 2004/050175 | 6/2004 |
| WO | 2004/093725 | 11/2004 |
| WO | 2004/105640 | 12/2004 |
| WO | 2005/009244 | 2/2005 |
| WO | 2005/065738 | 7/2005 |
| WO | 2006/092061 | 9/2006 |
| WO | 2006/105463 | 10/2006 |
| WO | 2006/130445 | 12/2006 |
| WO | 2006/138702 | 12/2006 |
| WO | 2007/064453 | 6/2007 |
| WO | 2007/121133 | 10/2007 |
| WO | 2007/124458 | 11/2007 |
| WO | 2008/072125 | 6/2008 |
| WO | 2009/029141 | 3/2009 |
| WO | 2009/067323 | 5/2009 |
| WO | 2009/111317 | 9/2009 |
| WO | 2009/115523 | 9/2009 |
| WO | 2009/132855 | 11/2009 |
| WO | 2010/009141 | 1/2010 |
| WO | 2011/029208 | 3/2011 |
| WO | 2011/079177 | 6/2011 |
| WO | 2011/101492 | 8/2011 |
| WO | 2011/103098 | 8/2011 |
| WO | 2012/030522 | 3/2012 |
| WO | 2012/125172 | 9/2012 |
| WO | 2013/048912 | 4/2013 |
| WO | 2013/177430 | 11/2013 |
| WO | 2014/013285 | 1/2014 |
| WO | 2014/060914 | 4/2014 |
| WO | 2014/207665 | 12/2014 |
| WO | 2015/047103 | 4/2015 |
| WO | 2015/075603 | 5/2015 |
| WO | 2015/079324 | 6/2015 |

* cited by examiner

IMPLANTABLE ULTRASOUND GENERATING TREATING DEVICE FOR BRAIN TREATMENT, APPARATUS COMPRISING SUCH DEVICE AND METHOD IMPLEMENTING SUCH DEVICE

This application is a Divisional of U.S. Ser. No. 15/536,996 filed on Jun. 16, 2017, which is a national phase of PCT/IB2015/002508 filed on Dec. 18, 2015.

TECHNICAL FIELD

The present invention relates to a device, an apparatus and a method for the treatment of brain disorders.

BACKGROUND ART

In the last decades, the academic and clinical knowledge and understanding of brain processes and diseases have considerably improved and so have the medical and surgical treatments of such pathologies. One field of brain medicine which has particularly developed is the field of neuromodulation techniques, which consist in submitting brain areas to a physical stimulation like an electric current or a magnetic field to treat a neurological disorder. Among neuromodulation techniques, DBS (which stands for "Deep Brain Stimulation") with electrical probes, TES (which stands for "Transcranial Electrical Stimulation") and TMS (for "Transcranial Magnetic Stimulation") are well known and exemplified in literature. U.S. Pat. No. 7,107,104 describes an implantable cortical neural lead for electrical stimulation of the cerebral cortex.

Recently, it has been proposed in WO 2006/092061 A1 implantable devices to cause lasting changes in neural functions through several types of physical stimulation (mechanical impulsion on cortex, electrical deep brain stimulation, drug infusion, for neurological deficit rehabilitation). It has also been suggested in WO 2009/067323 A1 devices for creating a skull/brain interface, which devices (implantable into the skull) are totally passive windows or channels permeable to external physical means (electric ionic current, radiofrequency . . . ) in order to neuromodulate brain activity for movement disorder or epilepsy pathologies.

In the field of brain cancer treatment, such neurostimulation techniques are not efficient. The treatments applied to this pathology remain the same as those applied for any kind of cancer, i.e. chemotherapies and/or surgical ablation of tumors when it is possible without irreversible or lethal damaging of the brain.

Surgical treatments of the brain require open surgical procedures in the skull of patients. Such open surgical procedures comprise a craniotomy, which includes performing a bone flap.

To do so, the surgeon firstly performs a trepanation in the skull by piercing several burr holes, and secondly unsticks the durra matter underneath. After that, the surgeon then performs the craniotomy by using a saw going from one burr hole to the other. Burr holes are usually 10 to 12 mm diameter each. The fragmented bone chip of each burr hole is kept and used at the end of the surgery to fill bone defects, which suffer poor, long-term, ossification. At the end of the surgical procedure, the bone flap is repositioned and fixed either with trans-skull stitches or with titanium micro-plates. The bone defect areas are filled up either with a synthetic copolymer or with bone powder obtained from the drilling of the burr holes at the beginning of the procedure.

Ultra keyhole surgical procedures do not require performing a bone flap, but only a burr hole. This burr hole can be very slight (4 mm diameter) in cases of stereotactic biopsy, but can be larger (between 8 to 12 mm diameter) for endoscopic procedures required for partial ablation of tumors.

Where chemotherapeutic treatments are concerned, these treatments include intravenous administration of highly active drugs to the patients. Unfortunately, these drugs are not specifically active onto the tumors and they also have considerable negative effects in the whole body of patients, with very unpleasant side-effects like nausea, hair loss etc. . . .

Known treatments of neurological and neurodegenerative diseases have limitations. Indeed, the brain is particularly difficult to deliver drugs to because of the blood-brain barrier (BBB). The impermeability of the BBB is due to the tight junctions connecting adjacent endothelial cells and highly regulatory transport systems of the endothelial cell membranes. However, these permeability properties pose tremendous obstacles when it comes to pharmacological treatment. The BBB prevents most neurologically active drugs from entering the brain and, as a result, has been isolated as the rate-limiting factor in brain drug delivery. Recently, local blood-brain barrier (BBB) opening has been found to be an advantageous approach for targeted drug delivery to the brain. It has been shown that localized ultrasound exposures, particularly when applied in the presence of intravenously injected gas bubbles, cause reversible opening of the BBB in targeted locations.

WO-2011/101492 describes a small rigid apparatus for the treatment of brain disorders which comprises an implantable generator having an ultrasound generating device positioned inside a casing and means for fastening the casing into the skull thickness. Such a device is well adapted for applications where a zone of the brain to be treated is of limited extension, for example less than 10 cubic centimetres. But several brain pathologies (i.e. diffuse gliomas, Alzheimer disease, . . . ) will require a much larger zone of treatment because the disease itself is diffused in the brain. WO-2011/101492 might not be adequate to address such an extension of the treatment zone.

U.S. Pat. No. 7,878,977 describes a flexible ultrasound transducer array for imaging applications. It discloses a condensed ultrasound transducer arrangement. Such a design is ideal for its ultrasound focusing properties, which is useful for imaging applications, but is not suitable for a diffuse unfocused treatment.

In fact, the present invention aims at offering an improved apparatus which can be used for addressing larger zones of the brain in view of providing treatments for brain tumors and other brain disorders (i.e. Alzheimer's Disease). Large zones may be addressed by an apparatus having several transducers. However, the presence of several transducers may be problematic in view of the risk that the ultrasound waves generated by such transducers may combine in such a way to create, locally in the treatment zone, unacceptably high pressures zones and/or the deposition of too much ultrasound power within a given tissue volume, resulting in unwanted or excessive heating of the tissue.

An originality of the present disclosure is based on an ultrasound device designed to be placed and slid under the skull on the brain and meninges surface.

According to an aspect, the invention provides for an apparatus for the treatment of brain disorders, comprising:
an implantable ultrasound generating treating device to induce brain disorder treatment by emission of ultrasound waves, wherein the implantable ultrasound generating treating device is suitable for implantation in or under the skull bone of a patient, wherein the implantable ultrasound generating treating device comprises an ultrasound emitting grid having several ultrasound generating transducers held by a common holder extending along a surface of extension, wherein the implantable ultrasound generating device comprises at least one group of several ultrasound generating transducers which are connectable by a common electrical connection circuit to a generator delivering electric drive signals driving the generation of ultrasound from the transducers, wherein the ultrasound generating transducers each have one or several operating frequencies, a generator to supply electricity to the implantable ultrasound generating treating device, characterized in that the group of transducers consists of several transducers which are commonly driven by a same electrical drive signal, and which are therefore connected to the generator system by a common electrical connection circuit of the implantable ultrasound generating treating device, where the electric drive signal serves both as power signal and as a control signal for operating selectively at least one or the other of a first transducer or sub-group of transducers within said group of transducers, and of a second transducer or sub-group of transducers within said group of transducers.

Thus, the same electric drive signal in the common electrical connection circuit of the implantable ultrasound generating treating device serves both as power signal and as a control signal for selectively activating at least one or the other of a first transducer or sub-group of transducers within said group of transducers, and of a second transducer or sub-group of transducers within said group of transducers.

According to an aspect, the invention provides an implantable ultrasound generating treating device to induce brain disorder treatment by emission of ultrasound waves, wherein the implantable ultrasound generating treating device is suitable for implantation in or under the skull bone of a patient, wherein the implantable ultrasound generating treating device comprises an ultrasound emitting grid having several ultrasound generating transducers held by a common holder extending along a surface of extension, wherein the implantable ultrasound generating device comprises at least one group of several ultrasound generating transducers which are connectable by a common electrical connection circuit to a generator system delivering electric drive signals driving the ultrasound generation of the transducers, and wherein the ultrasound generating transducers each have one or several operating frequencies.

The ultrasound generating transducers may comprise, within said at least one group of transducers, at least:
 a first ultrasound generating transducer or sub-group of transducers having at least a first operating frequency; and at least,
 a second ultrasound generating transducer or sub-group of transducers having at least a second operating frequency which is not an operating frequency of the first ultrasound transducer or sub-group of transducers.

According to another aspect, the invention provides an implantable ultrasound generating treating device to induce brain disorder treatment by emission of ultrasound waves, wherein the implantable ultrasound generating treating device is suitable for implantation in or under the skull bone of a patient, wherein the implantable ultrasound generating treating device comprises an ultrasound emitting grid having several ultrasound generating transducers held by a common holder extending along a surface of extension, characterized in that:
 the holder exhibits several holding zones on each of which are held one or several ultrasound generating transducers, and, between the holding zones, the holder exhibits flexing zones;
 the holder has a contour and has voids within the contour, between the holding zones and the flexing zones.

According to another aspect, the invention provides an implantable ultrasound generating treating device to induce brain disorder treatment by emission of ultrasound waves, wherein the implantable ultrasound generating treating device is suitable for implantation in or under the skull bone of a patient, wherein the implantable ultrasound generating treating device comprises an ultrasound emitting grid having several ultrasound generating transducers held by a common holder extending along a surface of extension, characterized in that:
 the holder exhibits several holding zones on each of which are held one or several ultrasound generating transducers, and, between the holding zones, the holder exhibits flexing zones;
 the holder exhibits differing flexibilities respectively around a first flexing axis and around a second flexing axis tangent to the surface of extension of the holder.

Typically said first and second flexing axis have directions forming an acute angle of at least 30°. More typically said first and second flexing axis have perpendicular directions.

Any of such apparatus and/or implantable device as above may further comprise one or several of the following features:
 The first operating frequency is not an operating frequency of the second ultrasound generating transducer or sub-group of transducers.
 The second operating frequency differs from the nearest operating frequency of the first transducer or sub-group of transducers by at least 10% of the second operating frequency.
 Each ultrasound generating transducer of a same group of transducers has an operating frequency different from any operating frequency of any other transducer of that group.
 On a given common holder, two transducers of a same sub-group are not adjacent. For example, at least one other transducer of another sub-group is closer to both of the said two transducers than the distance between said two transducers.
 An operating frequency of a transducer is a resonant frequency of the transducer.
 Each ultrasound generating transducer is connected to the common electrical connection circuit through a dedicated frequency selector circuit.
 The operating frequency of an ultrasound generating transducer is a resonant frequency of a dedicated frequency selector circuit through which the ultrasound generating transducer is connected to the common electrical connection circuit.
 Each ultrasound generating transducer is connected to the common electrical connection circuit through a dedicated frequency selector circuit passing frequencies inside a frequency band, and the operating frequency of the ultrasound generating transducer is comprised in the frequency band of its dedicated frequency selector circuit.
 The ultrasound generating transducers within the group of transducers are connected to the common electrical connection circuit through an implantable switch which is connected, upstream, to the common electrical connection circuit and, downstream, separately to several distinct sub-groups of one or several ultrasound generating transducers.

The implantable switch selectively connects the common electrical connection circuit to one of several distinct sub-groups of one or several ultrasound generating transducers, based on the electric drive signal which controls the implantable switch.

The implantable switch selectively connects in a sequence the common electrical connection circuit to one at a time of said several distinct sub-groups of one or several ultrasound generating transducers, based on the electric drive signal which controls the implantable switch.

The implantable switch generates a clock signal from the electric drive signal, said clock signal causing the switch to selectively connect in a sequence the common electrical connection circuit to one at a time of said several distinct sub-groups of one or several ultrasound generating transducers.

The implantable switch comprises a clock signal generator to generate a clock signal from the electric drive signal.

The implantable switch is energized from the electric drive signal.

The implantable switch generates a switch energizing signal from the electric drive signal, said switch energizing signal energizing the switch.

The implantable switch comprises a switch energizing signal generator to generate a switch energizing signal from the electric drive signal.

The implantable switch comprises:
- a digital counter having a control port and a set of output ports, where the control port receives a clock signal generated from the electric drive signal;
- a series of relays having each:
  - a power input port connected to the common electrical connection circuit to receive the electric drive signal;
  - a power output port electrically connected to one of said several distinct sub-group of one or several ultrasound generating transducers;
  - a gate port electrically connected to an output port of the digital counter.

The common electrical connection circuit of the implantable ultrasound generating treating device starts from an implantable connection receiver of the implantable ultrasound generating treating device and delivers electric signals to the transducers for driving the ultrasound generation of the transducers.

The ultrasound emitting grid is rigid.

The ultrasound emitting grid is flexible.

The holder comprises a unitary body of flexible material holding the ultrasound generating transducers.

The holder is made of at least one sheet of silicone based material.

The holder is made of at least one sheet of flexible material.

The holder comprises several sheets of material.

The implantable ultrasound generating device has, in front of at least some of the ultrasound generating transducers, an ultrasound conditioning device.

The ultrasound conditioning device is formed as a portion of the holder material which covers a frontal surface of an ultrasound generating transducer.

At least one of the ultrasound conditioning devices comprises one of a convergent lens, such as a convex lens, of a divergent lens, such as a concave lens, and/or of a diffracting array.

The electrical connection circuit comprises a connection receiver having a casing. In such a case, the connection receiver is preferably permanently connected to the implantable device, i.e. without possibility to electrically disconnect the transducers from the connection receiver. The casing may be rigid, or it may be semi-rigid.

The connection receiver casing is adapted to be fitted in a burr-hole performed in the skull of the patient to be treated.

The connection receiver casing is adapted to be fixed to the skull bone.

The implantable ultrasound generating treating device is made of non-ferromagnetic material.

The implantable ultrasound generating treating device is implantable through a burr hole.

The ultrasound generating transducers comprise elements chosen within the group formed by: piezo-composite elements, piezo-ceramic elements, C-MUT elements, or polyvinylidene difluoride (PVDF) elements.

According to another aspect of the invention, the invention relates to an apparatus for the treatment of a brain disorder comprising an implantable ultrasound generating device having any of the above features. Optionally, such an apparatus may further comprise one or several of the following features:

The apparatus comprises a generator system having a generator and a power controller to supply electricity to the implantable ultrasound generating treating device and to set and control its working parameters, and a connector to electrically connect the generator system and the implantable ultrasound generating treating device.

The generator delivers an electric drive signal which comprises selectively one or the other of:
- a first drive signal component having the first operating frequency; and of
- a second drive signal component having the second operating frequency;
in order to drive exclusively either one or the other of:
- the first transducer or sub-group of transducers; and of
- the second transducer or sub-group of transducers.

The generator delivers an electric drive signal which comprises both of:
- a first drive signal component having the first operating frequency; and of
- a second drive signal component having the second operating frequency;
in order to drive simultaneously both of:
the first transducer or sub-group of transducers; and of
the second transducer or sub-group of transducers.

The ultrasound generating treating device comprises ultrasound generating transducers with an operating frequency between 20 kHz and 200 MHz, more preferably between 500 KHz and 2 MHz.

The electrical connection circuit of the implantable ultrasound generating treating device comprises a connection receiver designed for cooperation with the connector of the generator system to achieve electrical connection between the generator system and the ultrasound generating treating device.

The connector of the generator system comprises one or several transdermal needles suitable for plugging into the connection receiver through the patient's skin.

The generator system comprises only one two-way transdermal needle or two one-way transdermal needles for operating selectively at least one or the other of the first transducer or group of transducers.

According to another aspect, the invention also relates to a method for treating brain disorders, characterized in that it comprises the steps of:

performing at least one opening into the skull of a patient, implanting through said opening an implantable ultrasound generating treating device, surgically closing the skin, connecting to the implantable ultrasound generating treating device to a generator system;

activating the generator for supplying power to said implantable ultrasound generating treating device and thereby inducing ultrasound wave emission into the brain, treating an area of the brain located beneath the implantable ultrasound generating treating device by ultrasound waves emission into the brain during a determined period, and deactivating the generator system when treatment is complete.

Such method may optionally further comprise one or several of the following steps or features:

The step of supplying power to said implantable ultrasound generating treating device includes a step of generating an electric drive signal comprising selectively one or the other of:

a first drive signal component having the first operating frequency; and of a second drive signal component having the second operating frequency;

in order to drive exclusively either one or the other of the first transducer or sub-group of transducers; and of the second transducer or sub-group of transducers.

The step of supplying power to said implantable ultrasound generating treating device includes a step of generating an electric drive signal comprising both of:

a first drive signal component having the first operating frequency; and of a second drive signal component having the second operating frequency;

in order to drive simultaneously both of:

the first transducer or sub-group of transducers; and of the second transducer or sub-group of transducers.

The step of supplying power to said implantable ultrasound generating treating device may include:

a step of generating an electric drive signal;

selectively connecting in a sequence the common electrical connection circuit through an implantable switch to one at a time of said several distinct sub-groups of one or several ultrasound generating transducers, based on the electric drive signal which controls the implantable switch.

The method may further include a step of injecting a contrast agent and/or a drug in the patient's blood before and/or during ultrasound emission in the brain, and emitting in the brain ultrasound waves with the implantable ultrasound generating device.

Said drug comprises therapeutic agents coated with ultrasound sensitive and/or thermal sensitive release/carrier agents, and in that the ultrasound waves emitted into the brain cause the release of the therapeutic agents only into the area of the brain receiving the ultrasound waves.

Ultrasound emission induces a loco regional release of ultrasound sensible release/carrier agents such as nanoparticles or liposomes for example.

Said contrast agent and/or drug injected in the patient's body is MRI-visible and its release within the brain is monitored by MRI after the ultrasound emission treatment.

Definitive or reversible sonoporation of the underneath cerebral tissue is carried out by ultrasound emission to increase drug input.

The positioning of the implantable ultrasound generating treating device is performed at the end of a regular tumor debulking open head neurosurgical procedure, by using existing craniotomy openings.

The method of the invention can be carried out at the end of a traditional neurosurgical procedure. The implantable generator is introduced in a burr hole performed in the skull of a patient or, when needed, in holes performed for a craniotomy procedure just before the skin closure of the patient. Such generating treating device emits ultrasound waves for treating the brain, for example an area of the brain previously accessed by the surgeon to treat a brain pathology, and for example a brain tumor.

The emission of ultrasound waves in the method of the present invention proves particularly efficient in providing blood brain barrier opening, which forms a first prominent application of said method. A second prominent application is to activate ultrasound sensitive nanoparticles. Other prominent applications include inducing slight continuous hyperthermia to induce vasodilation, stimulate local immunity, and/or activate thermosensitive nanoparticles. The implantable treating device being implanted under the patient's skull, the ultrasound energy emitted in the brain is not absorbed by the cranial bone wall.

Therefore, a method according to the invention may further include injecting at least one contrast agent in the patient's blood before or during ultrasound waves' emission to trigger and/or enhance opening of the haematoencephalic barrier (also called blood brain barrier, alias BBB) of the treated brain.

According to another advantageous characteristic of the invention, the method may further comprise a step of intravenously injecting a drug, such as an anti-tumorous drug, in the blood of a patient before, during, or immediately after ultrasound emission in the brain.

A drug thus injected may comprise therapeutic agents coated with ultrasound sensitive and/or thermosensitive release or carrier agents. In such a case, emitting ultrasound waves with the implantable treating device into the brain once the drug treatment has diffused in the patient's blood allows releasing the therapeutic agents only into the selected area of the brain to be treated, this area being defined as the area covered by the ultrasound emission.

In cases of cancerous lesions, intravenous systemic antitumorous chemotherapy is usually administered after surgery with products like Temodal (Registered Trademark) or Avastin (Registered Trademark).

However, the treatment of tumors is not the only application of the apparatus and method of the present invention. Indeed, ultrasound technology can be used to perform a broad spectrum of medical actions, which can be carried out together or alternatively with the method of the present invention. These complementary actions encompass:

Measuring intracranial physiological parameters like intracranial pressure, temperature, tissue elasticity . . . ;

Hyperthermia for enhancing blood vascularization and the enhanced permeability retention effect;

Local stimulation of immunity;

Local definitive or reversible sonoporation of the underneath cerebral tissue, especially of the cell membranes to increase drug input;

Combinations of any of the above described applications in the method of the invention with simultaneous contrast agent injection.

In addition to blood brain barrier, alias BBB opening, typical uses of the invention comprise the treatment with therapeutic effect of diffusing brain tumours, multiple brain metastases, Alzheimer's disease, diffuse neurodegenerative diseases, psychiatric disorders, drug resistant epilepsy.

BRIEF DESCRIPTION OF THE DRAWINGS

The apparatus and method of the present invention will be further described in detail below with reference to the accompanying drawings showing preferred embodiments of the apparatus of the invention.

In the Figures.

DESCRIPTION OF EMBODIMENTS

Figure 1:
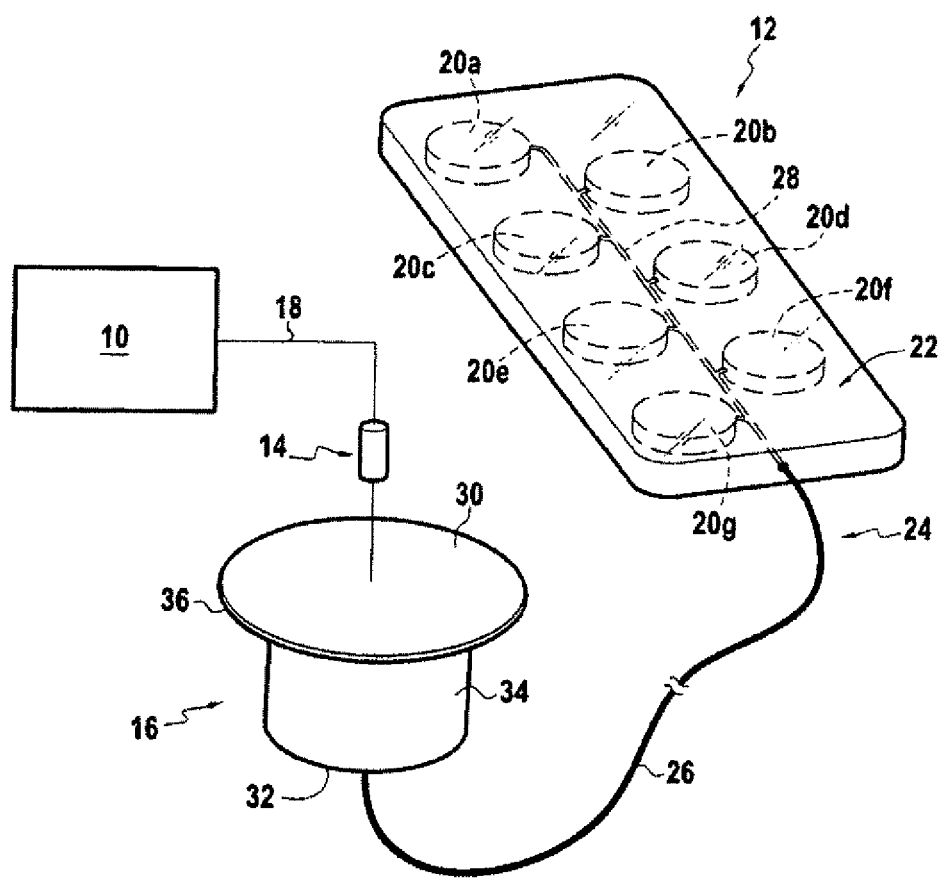
FIG. 1 represents schematically a first embodiment of the apparatus of the present invention.

On FIG. 1 are shown the main components of an apparatus for the treatment of a brain disorder, comprising an exemplary embodiment of an implantable ultrasound generating treating device 12 according to the invention.

This embodiment of an apparatus for the treatment of brain disorders comprises an extracorporeal generator system 10, which may for example have a generator and a power controller, to supply electricity to the ultrasound generating treating device 12 and to set and control its working parameters. According to an aspect of the invention, the implantable ultrasound generating treating device 12 is suitable for implantation under the skull of a patient, preferably under the skull bone, for example in the sub-dural space and/or at least partly in place of a portion of the dura-mater, whereas the generator system may be maintained external to the skull. In operation, the generator system 10 and the implantable ultrasound generating treating device 12 are to be connected electrically. Whereas such electrical connection could be achieved without contact, such as by inductive coupling, the electrical connection of the shown example is a more conventional cable connection. Such electrical connection could be permanent. However, in the shown embodiment of the invention, electrical connection is preferably achieved through a connector device 14 of the generator system 10 and a connection receiver 16 of the implantable device 12 which can be connected and disconnected. In the shown embodiment, the connector device 14 and the connection receiver 16 may be physically coupled to achieve electrical connection and may be decoupled without the need to remove the implantable device 12 from the skull of the patient. In this example, the connection receiver 16 thus forms a socket of a plug-and-socket connection, while the connector device 14 forms the plug of a plug-and-socket connection.

Preferably, the generator system 10 does not need to be adjacent to the head of the patient, including during operation of the apparatus. The connector device 14 may thus be connected to generator system 10 by a cable 18 having a suitable length allowing for example for the generator system 10 to be arranged near the patient's chest during operation of the apparatus. The cable may thus be at least 50 centimetres long, preferably longer than one meter.

The implantable ultrasound generating treating device 12 comprises several ultrasound generating transducers 20 held by a common holder 22 extending along a surface of extension. The ultrasound generating transducers 20 and the common holder 22 form together an ultrasound emitting grid. The ultrasound generating transducers 20 are arranged on the common holder 22 so as to be spread, preferably at regular intervals, along most of the surface of extension of the ultrasound emitting grid. The ultrasound generating transducers 20 are preferably spaced apart from each other by a non-zero distance on the common holder. The implantable ultrasound generating treating device 12 also comprises an electrical connection network for connecting the ultrasound generating transducers 20 to the generator system 10 delivering electric drive signals. In the shown embodiment, the electrical connection network starts from the connection receiver 16 and delivers electric signals to the transducers for driving the ultrasound generation of the transducers. As will be understood below, an electric drive signal may serve both as power signal and as a control signal. The electric connection network may comprise one or several electrically independent electric connection circuits 24, where it will be understood that a given electric connection circuit 24 is a circuit where a common electric drive signal is circulating. Preferably, as will be described below, the electric connection network will comprise only one independent electric connection circuit 24, so that the electric connection between implantable ultrasound generating device 12 and the generator system, here through the connector 14 and the connection receiver 16 can be made as simple as possible. Indeed, in such a case, only one two-way connection will be needed, with one electrical channel for the signal connection and one electrical channel for the ground return. However, the electric connection network may comprise several independent electric connection circuits. This may be useful for example in case of a great number of transducers or in a case where the implantable ultrasound generating device 12 comprises several independent holders. In such a case, each independent electric connection circuit will have its own independent electric connection to the generator system 10 and the generator system may deliver separate and different electric drive signals to each independent electric connection circuit.

In the shown example, the connection receiver 16 is separate from the holder 22. Therefore, the electric connection circuit 24 comprises at least one cable 26, most commonly made of one pair of wires where one wire corresponds to one independent electrical channel, which extends from the holder 20 to the connection receiver 16. Preferably, there is a single cable 26, although it may comprise several electrically separate wires bundled together. On the holder 22, the cable 26 of electric connection circuit 24 separates into connection lines 28 for delivering an electric drive signal to the individual transducers 20 of a given group of transducers. A group of transducers will be defined as several transducers which are commonly driven by a same electrical drive signal, and which are therefore connected by a common electrical connection circuit 24 to the generator system. In the shown embodiment, the connection lines 28 form ramifications of a single electric circuit which is common for one group of transducers, as illustrated in FIG. 1.

The connection lines 28 can be mounted on a surface of the holder 22 or can be at least partly, but preferably fully, embedded in the holder 22, thus forming part of the ultrasound emitting grid.

Figure 13:
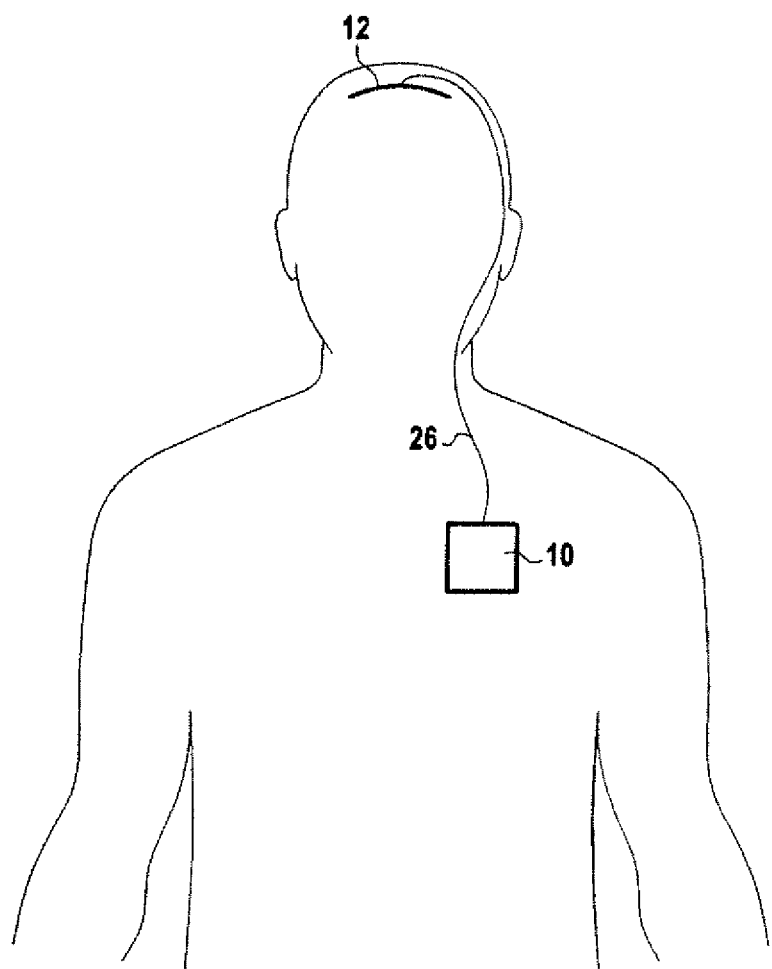
FIG. 13 represents schematically an example of the implantation of an apparatus according to the invention, comprising an implantable generator.

It must be noted that, as shown in the example of FIG. 13, the generator 10 and preferably the entire generator system could also be implantable. It could be implanted in the chest of a patient. In such a case, the implantable ultrasound generating device 12 and the implantable generator 10 could be electrically connected by a cable with at least one disconnectable connection, such as a plug- and socket connection. The cable 26 could be implanted within the patient's body, along all its length from the ultrasound generating device 12 and the implantable generator 10, i.e. under the skin. The cable could be permanently connected to the ultrasound generating device 12 and could comprise a plug to be connected on a socket of the generator. However, the cable could also be, in part, external to the body between the implantable ultrasound generating device 12 and the implantable generator system.

Figure 2:
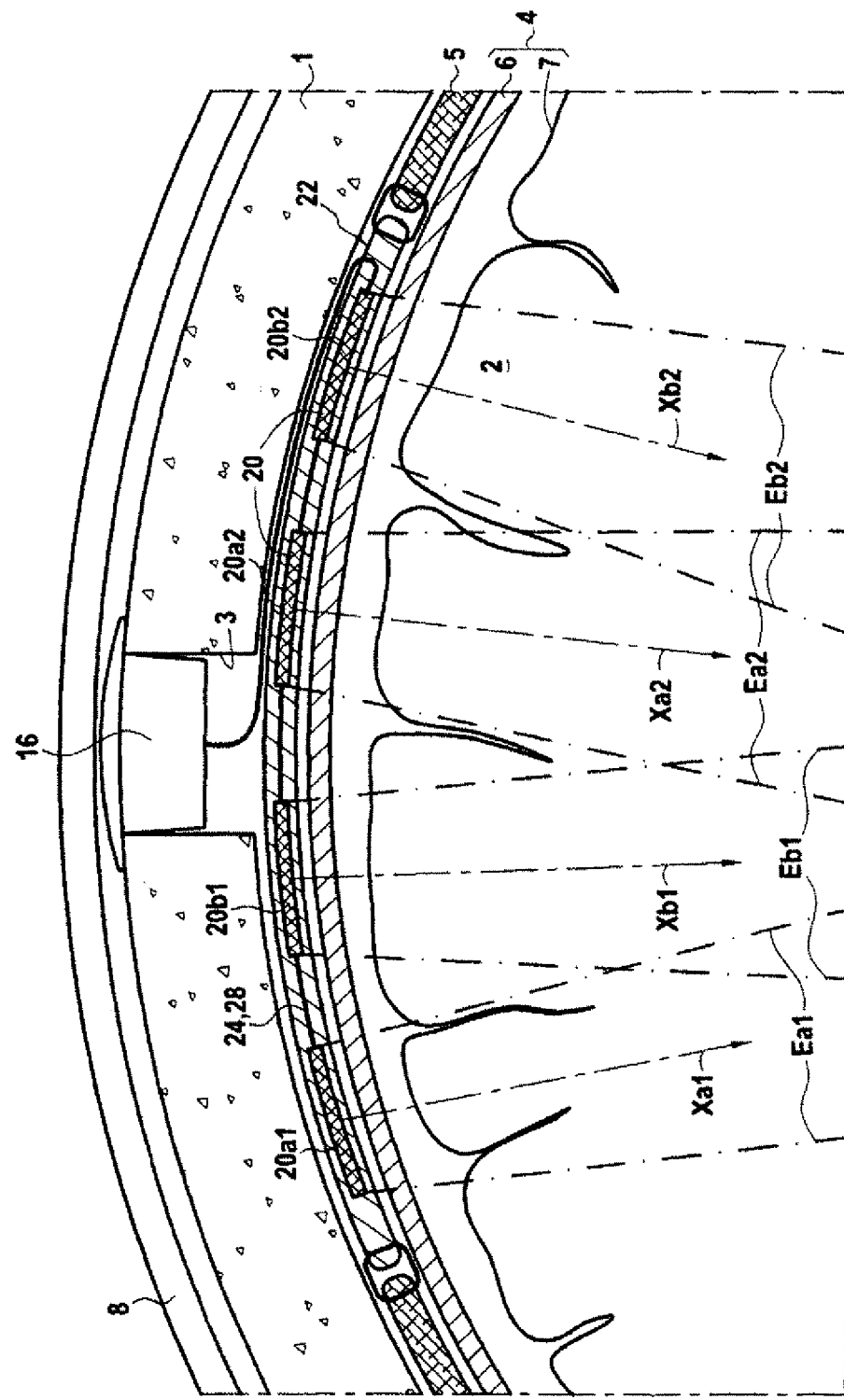
FIG. 2 represents schematically an example of the implantation of a device according to the invention in the head of patient.
Figure 3:
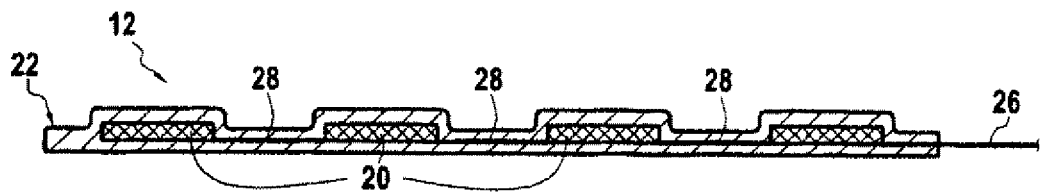
FIGS. 3 to 6 represent various variants of an ultrasound emitting grid for a device according to the invention when viewed in cross section.

The enclosed FIG. 2 is a schematic section view of a portion of an animal or human head where have been represented the skull bone 1, covering the brain 2, into which a burr hole 3 has been drilled to perform a regular craniotomy. Between the skull 1 and the brain 2, one will recognise the presence of the meninges 4 which may typically include, from the skull 1 to the brain 2, the dura-mater 5, the arachnoid mater 6 and of the pia mater 7.

According to an aspect of the invention, the holder 22 and its ultrasound generating transducers 20 is to be implanted under the skull, preferably under the skull bone 1. As will be seen more in detail, the connection receiver 16 is of course implantable in the skull, but it may more particularly, as shown in FIG. 2, be designed to be received within the aperture of the burr hole 3. However, the connection receiver is preferably to be located below the skin 8 which covers the skull.

In the shown embodiment, the holder 22 extends along a surface of extension which is preferably parallel, or essentially parallel, to an internal surface of the skull bone 1. The holder 22 is an element which holds several ultrasound generating transducers 20 which are to be located at different locations along the surface of extension of the holder. Preferably, the holder 22 is able to maintain a relative distance between the various transducers 20. However in the case of the illustrated embodiment, due to the fact that, as will be explained below, the holder 22 exhibits some flexibility, the holder 22 may allow some amount of displacement between the transducers 20 it holds.

Alternatively to the shown embodiment, the ultrasound emitting grid may be a rigid system such as the exemplary embodiments described in WO-2011/101492. In such a case, the grid may be received in a burr-hole made in the skull bone. This grid is then received at least in part within the thickness of the skull bone. As another example, the holder shown in the figures of this application could be rigid, i.e. not flexible.

However, according to an aspect of the illustrated embodiment of the invention, the holder 22 is advantageously flexible. As a consequence, the ultrasound emitting grid as a whole, including the ultrasound generating transducers 20 and, when applicable, the connection lines 28 for delivering electric current to the individual transducers, is flexible.

According to a desirable feature deriving from that flexibility, the holder 22 and the ultrasound emitting grid are preferably manually deformable between at least a first spatial configuration, or shape, to at least a second spatial configuration or shape, meaning that, before its implantation or during its implantation, the holder 22 may be deformed to a desired shape by the mere application of biasing or deformation forces which are comparable to those which may be easily applied by hand. Typically, for an ultrasound emitting grid to be considered as flexible, a surgeon implanting such ultrasound emitting grid should be able to deform the holder 22 to give it a certain spatial configuration without resort to any kind of tool. This does not prevent however that deformation and/or implantation of the holder 22 can be deformed/implanted using tools typically employed in brain surgery, especially tools for performing remote-control surgery.

Preferably, the holder 22, and thus the ultrasound emitting grid, is reversibly deformable such that, after it has been deformed from a first spatial configuration to a second spatial configuration, it can be deformed back to its first spatial configuration or very near to such spatial configuration.

Preferably, the amount of manual reversible deformation of the holder 22, and thus of ultrasound emitting grid 12, which may be obtained is substantial, meaning optically visible with the naked eye. The amount of manual reversible deformation possible for a given holder may be evaluated as a deformation percentage X %. This deformation percentage X % can be evaluated as follows: for at least two locations of the holder 22 which are distant by L mm along a direction in the surface of extension of the holder 22, the two locations of the holder 22 can be displaced one with respect to the other along a direction perpendicular to the surface of extension of the holder 22, by manual reversible deformation, by a distance of at least L×X % mm. Preferably, the amount of manual reversible deformation is at least of 10%, more preferably of at least 25%. As an example, in the case of a deformation percentage of at least 10%, for two locations which are 100 mm apart along the surface of extension of the holder, the possible manual reversible deformation should be of at least 10 mm along a direction perpendicular to the surface of extension.

In a preferred embodiment, the ultrasound emitting grid is flexible enough to be folded on itself by manual deformation so that two opposite borders of the holder may be brought into contact.

In a preferred embodiment of the invention, the holder 22, and thus the ultrasound emitting grid, is manually reversibly deformable between a non-finite number of spatial configurations, meaning that the deformation is continuous and not step by step.

In some embodiments, the holder 22 and/or the ultrasound emitting grid may be conformable, meaning that it is not entirely elastic and maintains a certain deformation even after any significant biasing or deformation force has been stopped. In such a case, the holder 22 may be deformed from an initial spatial configuration to a temporary spatial configuration upon application of a biasing or deformation force, and then may attain a final spatial configuration upon release of the biasing or deformation force. The deformation of the final spatial configuration compared to the initial spatial configuration is nevertheless preferably substantial, i.e. optically visible with the naked eye, preferably with a deformation percentage of at least 10%, preferably more that 25%. If the holder 22 has a low degree of elasticity, the deformation of the final spatial configuration compared to the temporary spatial configuration (i.e. the spring back deformation) is for example less than one fourth of the deformation amount between the initial and the temporary spatial configurations, for example less than on the tenth. Preferably, such holder 22 is conformable in a non-finite number of spatial configurations. The conformability of the ultrasound emitting grid may result for example from the conformability of the electric connection lines 28 which may be non-elastic for the deformations which are envisioned for the ultrasound emitting grid while the holder 22 in itself may be somewhat elastic.

In some embodiments, the holder 22 and/or the ultrasound emitting grid may be elastic and may thus have at least one stable spatial configuration to which it returns or tends to return when non-biased. More precisely, as perfect elasticity does not exist, such elastic ultrasound emitting grid should return to a spatial configuration close to the initial spatial configuration, with a residual deformation between the final deformation and the initial deformation which is, after application of the biasing or deformation effort has ceased, preferably less than 10%, more preferably less than 5%. Such elasticity is preferably maintained after a temporary deformation of up 25%, preferably up to 40%. Elasticity of the ultrasound emitting grid as a whole may derive from elasticity of the connecting lines, while the holder in itself could be substantially non elastic or ultra-flexible as defined hereunder.

In the case of an ultrasound emitting grid exhibiting at least some elasticity, the stable spatial configuration may be a flat configuration where the surface of extension of the holder extends essentially along a plane. However, the stable spatial configuration may be three dimensional, for example exhibiting a dome shape. In such a case, the surface of extension of the holder 22 may be configured as a three dimensional surface, for example as a dome (see FIG. 9).

In some embodiments, the ultrasound emitting grid, and thus the holder 22, may be ultra-flexible, i.e. exhibiting a very low degree of rigidity. Such an ultrasound emitting grid cannot hold its own weight. For example, a flat ultrasound emitting grid will be considered ultra-flexible if, along at least one test direction, when the ultrasound emitting grid is clamped at one extremity of the holder so that the clamped extremity extends substantially horizontally, the holder exhibits, by virtue of its sole weight, at least 50% of deformation between the clamped extremity and the free opposed extremity along that direction, meaning that the vertical deflection of the free opposed extremity is at least 50% of the length of the holder between its two extremities along that direction. Such an ultra-flexible ultrasound emitting grid will have the advantage of generating the least possible pressure on the brain which may be due to its deformation. Such ultra-flexible holder may also be defined by the fact that it automatically adopts the shape of a surface it is in contact with, without generating any pressure, or at least without generating any substantial pressure, which pressure would be due to its own elasticity. Of course, it may generate some pressure, for example due to its weight, and/or due to its thickness if sandwiched between two surfaces. In such a case, not only the holder 22 should be ultra-flexible, but also the electric connection lines 28, if any, should not impair the ultra-flexibility of the ultrasound emitting grid as a whole.

In some embodiments, the holder 22 comprises a unitary body of flexible material holding the ultrasound generating transducers. A body can be considered unitary if it exhibits continuity of matter along it surface of extension. Preferably, such unitary body is a single unitary body holding all the ultrasound generating transducers.

The holder 22 may be in the form of at least one sheet of flexible material extending along the surface of extension. Such a sheet exhibits a thickness which preferably has a maximal value less than at least 4 times the smallest of the other two dimensions of the sheet, more preferably less than 8 times the smallest of the other two dimensions. For example, the thickness of the sheet could be in the order of 1 to 4 mm, such as 2 mm.

Figure 4:
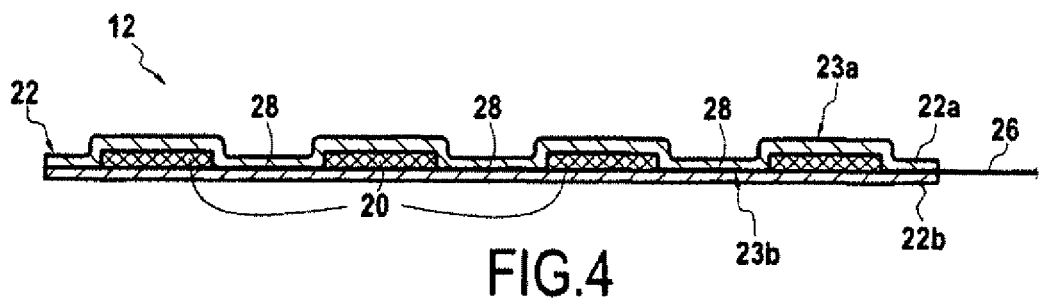
Figure 5:
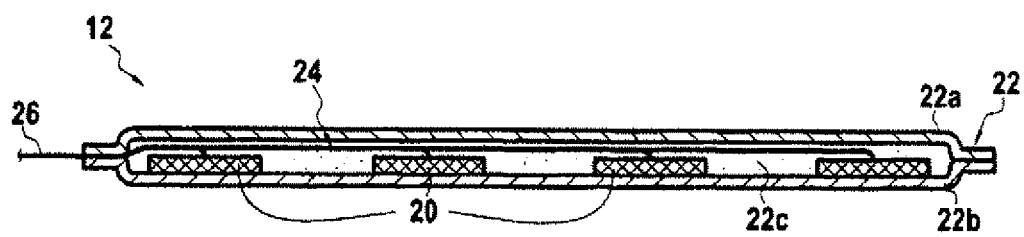

The holder 22 may be in the form of at least two sheets of flexible material which extend one along the other, across at least a substantial portion of the surface of extension of the holder, i.e. with preferably over 70% of overlap, more preferably more than 80% of overlap (see FIG. 4 and FIG. 5). In such a case, despite the fact that the holder has different layers, possibly, the holder may be considered unitary as the various sheets which largely overlap are themselves unitary across the surface of extension.

The sheet or sheets of flexible material may be planar or may extend along a three-dimensional surface.

Preferably, the holder 22 is made of at least one sheet of elastomeric material, such a silicone based material, preferably of medical grade. Silicone based materials are materials of choice considering their biocompatibility and their softness to avoid brain traumatism.

In the case of multiple sheets, the different sheets can be of a same material or of different materials, for example different grades of material. For example, as shown on FIG. 4, the holder 22 may comprise an upper sheet 22a, on the skull bone side of the holder and made of a first grade of silicone, and a lower sheet 22b, on the brain side of the holder and made of a second grade of silicone. For example, the second grade of silicone may be softer than the first grade, i.e. for example exhibiting a lower shore A hardness, and/or the first grade may be selected to exhibit a higher toughness by exhibiting a higher degree of resistance to tearing. According to another example illustrated in FIG. 5, the different sheets of material may include a central sheet 22c of a first elastomeric material on which the ultrasonic generating transducers may be fixed and two external sheets 22a, 22b of a second elastomeric material, the two external sheets fully encapsulating the central sheet and the ultrasonic generating transducers. In such a case, the first material may exhibit a relatively higher toughness to tearing than the second material, and/or the second elastomeric material may exhibit a relatively higher degree of biocompatibility than the first material.

Typically, the unitary body of flexible material will exhibit several holding zones 23a on each of which one or several ultrasound generating transducers are held, and, between the holding zones, the unitary body exhibits flexing zones 23b. In such a case, the flexing zones are manually reversibly deformable. The flexing zones may comprise portions of reduced thickness of the unitary holder. In the case of a multi-sheet construction of the holder 22, the flexing zones may be zones where one of the sheets is absent.

Figure 6:
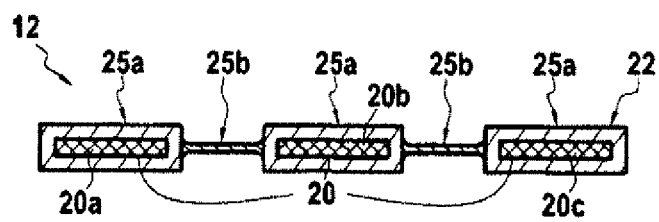

In other embodiments, such as illustrated in FIG. 6 the holder 22 may be non-unitary and may comprises several rigid holding portions 25a, i.e. not suitable for manual reversible deformation, and on each of which one or several ultrasound generating transducers are held, and the rigid holding portions may be connected by articulation portions 25b. It is to be understood that in such case, at least two distinct rigid portions hold each respectively one of at least two distinct ultrasound generating transducers. The articulation portions may be made with a mechanical connection, such as a pivot or ball joint connection, but, as illustrated in FIG. 6, are preferably made of flexible material, thus forming a flexing portion.

In any case, the holding portions may exhibit rigidity by themselves and/or may become due to the rigidity of the transducers they hold.

The holder 22 preferably comprises attachment portions for attaching the holder, and thus the ultrasound emitting grid, for example to the dura-mater. Such attachment portions are preferably located on the periphery of the surface of extension of the holder. The holder 22 may be attached by stitches (as illustrated in FIG. 2) or by screws, but also possibly by riveting or by gluing with a biocompatible glue. In one example, the ultrasound emitting grid is fixed by the holder attachment portions being stitched to the dura-mater.

Preferably, the ultrasonic transducers 20 are sealed inside the holder 22 in a watertight manner, for example by being embedded in a flexible material of the holder, or by being encapsulated between two layers of flexible material. Preferably also, the part of the electric connection circuit 24 which is held on the holder 22, i.e. the connection lines 28, is also embedded or encapsulated in the holder 22.

In the example of FIGS. 1 and 2, the holder 22 is a unitary holder which exhibits a single sheet of elastomeric material. The holder is initially flat, in that, if supported on a flat surface, it exhibits a flat surface of extension. It exhibits for example a flat upper surface and a flat lower surface. The ultrasonic transducers 20 are arranged inside the volume of the holder 22, which is in this case composed of a single sheet of material, in this case a medical grade of silicone based material. In this example, the holder has a rectangular contour in the surface of extension. However, other shapes could be possible, including common geometrical shapes (square, circle (see FIG. 7), ellipse, . . . ) or irregular shapes.

On the holder 22, the ultrasound generating transducers 20 may be arranged according to any pattern. In some embodiments, all transducers 20 may be aligned along a same line. However, it is preferred that the transducers are arranged so as to form a two dimensional arrangement extending in the surface of the extension. Advantageously, the transducers may be arranged as in a quincunx. For example, in the embodiment of FIG. 1, the transducers are arranged along two parallel rows extending along a longitudinal direction, the two rows being spaced laterally along a transversal direction. In this embodiment, the transducers are regularly spaced along the longitudinal direction in each row. However, the longitudinal position of the transducers in one row is offset longitudinally compared to the longitudinal position of the transducers in the other row, thus forming a quincunx-like arrangement.

In the examples shown on FIGS. 1 to 11B, the holder exhibits no voids within its contour.

However, the holder could have voids within the contour, between the holding zones and the flexing zones. For example, as in the example of FIGS. 14 to 16, the holding zones which hold the transducers could be linked to each other by flexible arm portions, voids being delimited between such flexible arm portions. In this example, the holding zones 23a carry only one ultrasonic transducer 20 each. In the case of ultrasonic transducers 20 having a circular cross-section, as shown on FIG. 14, the holding zones 23a can have an annular shape surrounding the corresponding ultrasonic transducer 20.

Figure 14:
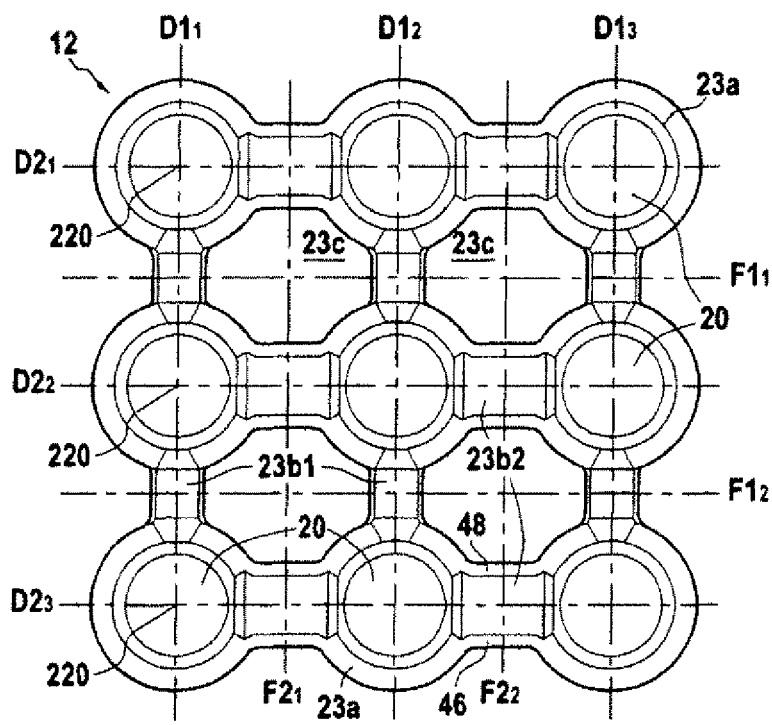
FIGS. 14, 15 and 16 represent schematically a further embodiment of an implantable ultrasound emitting grid according to the invention.
Figure 15:
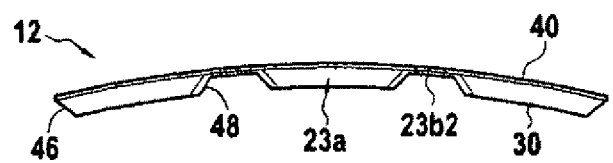
Figure 16:
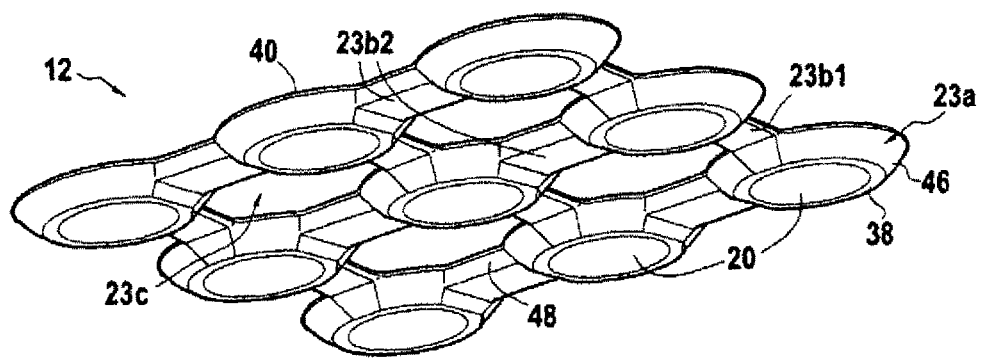

In the example of FIGS. 14 to 16, the holding zones 23a, and thus the ultrasonic transducers 20, are arranged along a grid forming several parallel columns $D1_1$, $D1_2$, $D1_3$, along a first direction D1 and several parallel rows $D2_1$, $D2_2$, $D2_3$ along a second direction D2. In this case, the first and second directions D1, D2 are perpendicular. In a variant having transducers arranged along a quincunx, the first and second directions could form an acute angle of 45° or lower, preferably however forming an acute angle of more than 30°. In the shown example, there are three transducers per row and three transducers per column, but more transducers or less transducers could be provided along a row, along a column or along both.

In the example of FIGS. 14 to 16, each holding zone 23a in a row $D2_1$, $D2_2$, $D2_3$ is connected to the adjacent holding zone 23a in the same row by flexing zone 23b in the form of a flexible arm portion extending along the second direction D2. Also, each holding zone 23a in a column $D1_1$, $D1_2$, $D1_3$ is connected to the adjacent holding zone 23a in the same column by a flexing zone 23b in the form of a flexible arm portion extending along the second direction. Voids 23c are delimited between such flexible arm portions. Voids 23c have a closed perimeter along the surface of extension of the holder.

According to another aspect of the invention, the holder 22 as a whole may exhibit differing flexibilities respectively around a first flexing axis $F1_1$, $F1_2$, having a flexing axis direction F1, and around a second flexing axis $F2_1$, $F2_2$, having a second flexing axis direction F2, both tangent to the surface of extension of the holder 22, the said first and second flexing axis forming an acute angle of at least 30°, preferably forming an angle of 90°. In other words, the holder 22 as a whole, with its transducers 20, can be more easily flexed to a globally cylindrical or convex shape around the first flexing axis direction F1, than around the second flexing axis direction F2.

For example, as in some of the embodiments described above, the holder 22 may exhibit several holding zones 23a on each of which are held one or several ultrasound generating transducers 20, and, between the holding zones 23a, the holder exhibits flexing zones 23b. The flexing zones may be configured so that the holder as a whole can be more easily flexed around one flexing axis direction, for example the first flexing axis direction F1, than around the other flexing axis direction, for example the second flexing axis direction F2.

For example, the holder 22 may have:
- a first flexing zone 23b1 extending along a first direction D1, perpendicular to the first flexing axis direction F1, from a given holding zone 23a to a first adjacent holding zone 23a.
- a second flexing zone 23b2 extending along a second direction D2, perpendicular to the second flexing axis direction F2, from said given holding zone 23a to a second adjacent holding zone 23a distinct from the first adjacent holding zone 23a.

The first and second flexing zones 23b1, 23b2 may, as in the example shown on FIG. 14, exhibit differing flexibilities respectively around the first flexing axis direction F1 and around the second flexing axis direction F2.

In FIG. 14, the first flexing zones 23b1, arranged along the columns, are more flexible than the second first flexing zone 23b2, arranged along the rows.

The differing flexibilities can derive from the material of the respective flexing zones, their geometry (cross-section perpendicular to their direction of extension, length along their direction of extension, presence of reinforcements, . . . ).

In the example of FIG. 14, the given holding zone and the first and second adjacent holding zones hold each only one ultrasound generating transducer. Therefore, the centre 220 of the corresponding transducer 20 defines a centre of the holding zone.

As an example, the flexibility of the first and second flexing zones 23b1, 23b2 may be compared by:
- maintaining the given holding zone horizontal, as defined by a plane tangent to the surface of extension at the centre 220 of the given holding zone;
- applying a given force on the centre 220 of the first adjacent holding zone, along a force direction perpendicular to the surface of extension of the holder at the centre of the first adjacent holding zone and measuring the deflection of said centre along said force direction;
- applying the same given force on the centre of the second adjacent holding zone, along a direction perpendicular to the surface of extension of the holder at the centre of the second adjacent holding zone and measuring the deflection of said centre along said direction
- comparing the respective deflections.

Figure 10:
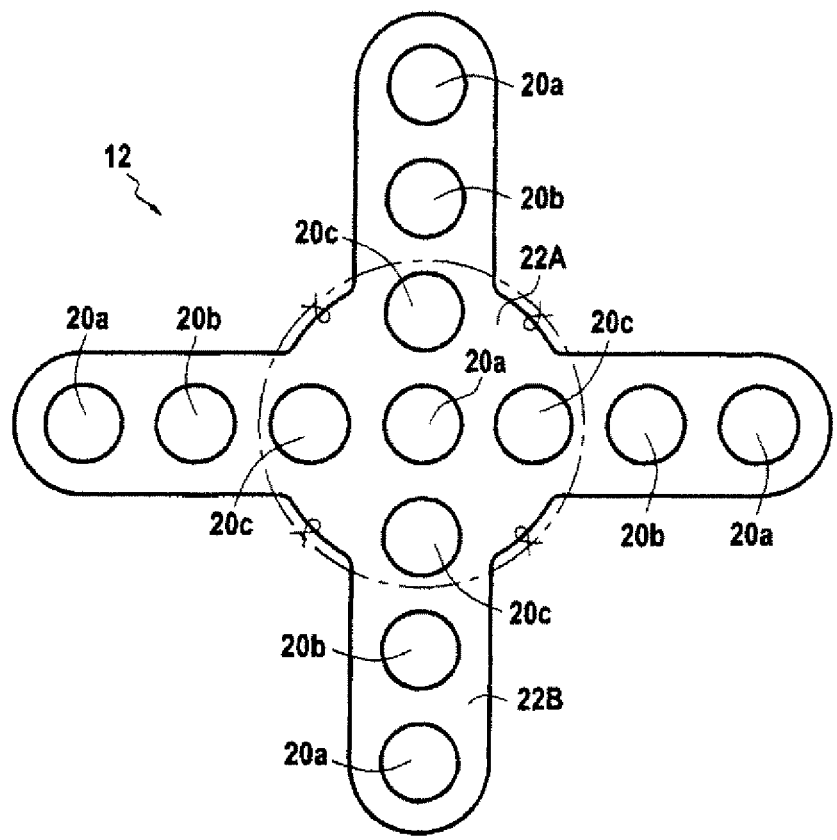
FIG. 10 represents a schematic top view of a further variant of a grid for a device according to the invention.

The contour in the surface of extension may be entirely convex or may exhibit concavities. For example, the contour of the holder may resemble that of a flower with fully or partially separated petals (see FIG. 8). As another example of a surface of extension exhibiting concavities, the embodiment of FIG. 10 exhibits a holder 22 which has central portion 22A, which may be circular as shown, but which could be elliptical or of any other known convex shape, and radial portions 22B which extend radially from a central portion. Each of the central and radial portions 22A, 22B preferably hold ultrasound generating transducers 20. The various radial portions of a given holder may be all similar, or at least some of them may be dissimilar. For example radial portions 22B exhibit a certain length along their radial direction of extension, which length may be equal for each radial portion 22B, or may be dissimilar for at least some radial portions 22B. Radial portions 22B may be distributed evenly angularly around the central portion 22A, as shown in the embodiment of FIG. 10, or could be distributed unevenly. Each radial portion 22B exhibits a width, perpendicularly to its respective radial direction of extension, which may be constant along its length, or which may to the contrary increase or decrease along with increased distance from the central portion 22A along the radial direction. In the shown embodiment of FIG. 10, the radial portions 22B exhibit a constant width except at their terminal portions which are rounded. The central and radial portions may exhibit the same thickness, perpendicularly to the surface of extension of ultrasound emitting grid, or may be of different thickness. For example, the central portion 22A of the ultrasound emitting grid may be thicker than the radial portions 22B. In such a case, the ultrasound emitting grid may implanted under a patient's skull with the central portion being received in a location where the dura-mater has been removed, whereas the radial portions may be received between the meninges, including the dura-matter and the brain.

As exemplified in FIGS. 5, 11A, 11B and 15, the holder 22 may have a bevelled contour edge to limit the physical pressure on the brain and may help inserting the device over the patient's brain.

In the example of FIGS. 14 to 16, the holder 22 exhibits:
- a lower surface intended to be installed facing the brain
- an upper surface opposite the lower surface
- a bevelled contour edge forming a bevel 46 turning away from the upper surface.

With such a bevel turning away from the upper surface, the lower surface facing the brain is of lesser area than the upper surface.

Figure 11A:
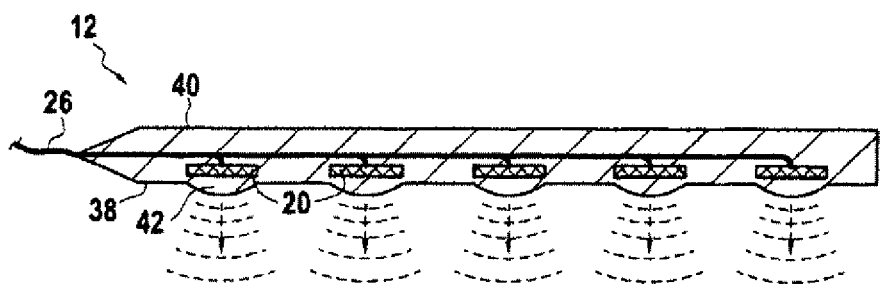
FIGS. 11A and 11B represent two further variants of an ultrasound emitting grid for a device according to the invention when viewed in cross section.
Figure 11B:
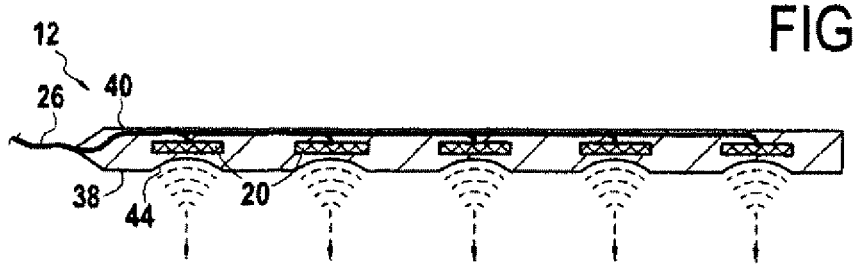

The bevel 46 may, as visible on FIG. 16, extend along the entire contour of the holder, or, as shown on FIGS. 11A, 11B on only part of said contour.

In the same way, if the holder comprises voids 23c, such voids 23c may have a bevelled perimeter, as visible on FIG. 16. Preferably, the perimeter of each void 23c is bevelled along its entire length. Preferably, the bevelled perimeter of the void 23c forms a bevel 48 turning away from the upper surface.

The bevels 46, 48 are preferably surfaces which intersect with the upper surface 40 where the holder 22 forms an acute angle between said bevel 46, 48 and said upper surface 40, preferably comprised between 25 and 75 degrees.

When the holder 22 is installed under the skull, it will adapt its curvature to the brain's curvature. Then distinct transducers could converge and emit ultrasound in the same area of the brain, leading to an undesired superposition of their ultrasound emission. Such ultrasound beam superposition may in such a case generate zones of undesired increased peak pressure that could modify the therapeutic effect and then bring safety issues.

According to an aspect of the invention, for a given implantable ultrasound generating device 12, a given group of ultrasound generating transducers 20 may comprise at least two subgroups of transducers which may be differentiated by the transducers in the two different sub-groups having different operating frequencies. Transducers of a same sub-group preferably have a same operating frequency.

An operating frequency of a given transducer 20 is a frequency for which it delivers a higher acoustic power output for a given electric drive signal power, compared to the acoustic power output delivered at neighbouring frequencies. It must be noted that the term operating frequency, as used in this text, covers an individual peak operating frequency, at which the transducer 20 delivers a peak ultrasound field power/intensity for a given electric drive signal power, or an operating frequency range, around such peak power frequency, for which the transducer 20 delivers a ultrasound field power/intensity higher than a minimum field power/intensity, which may be expressed as a percentage of the peak ultrasound field power/intensity.

In some embodiments, each ultrasound generating transducer 20 may be connected to the common electrical connection circuit 24 through a dedicated frequency selector circuit, such as a filter, typically a band-pass filter passing frequencies inside a frequency band and attenuating the frequencies outside the band. In such a case, the operating frequency of the ultrasound generating transducer may be comprised in the frequency band of its band-pass filter. For example, the frequency selector circuit filter may tune the transducer's electrical impedance to 50 ohms within a narrow frequency band so that when driven using a long connection cable and connected to the generator, the transducer is driven efficiently, i.e. with minimal electrical losses. The dedicated frequency selector circuit may be individual for a given ultrasound generating transducer 20. The dedicated frequency selector circuit may be common for several ultrasound generating transducers 20. The dedicated frequency selector circuit may be common for all of the ultrasound generating transducers 20 of a given sub-group of transducers.

In some embodiments, an operating frequency of a given transducer may be a resonant frequency of the transducer. Indeed, in most commonly used ultrasound generating transducers 20, the ultrasound energy is generated by virtue of the vibration created in the core of the transducer by an alternating voltage by virtue of a piezoelectric effect or capacitive variation. The transducer is fed with an electric voltage which may have a given frequency or which may have a frequency spectrum which may be decomposed into preferably a limited number of main frequencies. The core of the transducer may thus be designed such that it exhibits at least one inherent resonant frequency. A resonant frequency of the transducer can be defined as the frequency of the drive signal for which the ratio of the acoustic power output divided by consumed electrical power reaches a maximum (at least within neighbouring frequencies). For a typical piezoceramic transducer, this ratio is typically between 50% and 90% at a resonant frequency. If the electric current fed to the transducer exhibits such frequency, it will induce in the transducer a resonant vibration which will generate ultrasound. If the electric current fed to the transducer exhibits only a frequency or frequencies which lie outside of an operating range around the operating frequency, then the acoustic power output will be less than 25% of the power delivered when driven with a given voltage at its operating frequency.

A transducer may have a given operating frequency by choosing for example its resonant thickness mode for a piezoceramic material, e.g. 2 mm thickness for a 1 MHz transducer for PZ26 material. Thus, a transducer with a resonance of 0.9 MHz may be constructed by using a transducer made of such material with a thickness of 2.2 mm or a transducer with a resonance frequency of 1.1 MHz may be constructed by using a transducer made of such material with a thickness of 1.8 mm. Alternatively, a matching layer that is glued to the front face of the transducer may be used to ideal couple the ultrasound energy into the tissue at a given operating frequency.

The operating frequency of a transducer may alternatively be defined by being a resonant frequency of a dedicated frequency selector circuit through which the transducer 20 may be connected to the common electrical connection circuit 24.

Preferably, the second operating frequency, which is specific to the second sub-group of transducers differs from the nearest operating frequency of the first transducer or sub-group of transducers by at least 10% of the second operating frequency. If the operating frequency covers an operating frequency range, such range should be of limited extent and two operating frequency ranges should not overlap. Such a feature will ensure that there is a sufficient separation between the operating frequencies so that one of the sub-groups may be activated while the other will not be activated. Indeed, activation of a transducer is triggered by the frequency content of the electric drive signal delivered to the transducer. If the electric drive signal contains the operating frequency of the transducer, the transducer is activated and delivers an ultrasound field. If not, the transducer is not activated.

The frequency content of the electric drive signal can be obtained directly, in case of a simple alternating voltage having one frequency, such as a pure sinusoidal signal. It can also be obtained through Fast Fourier Transform (FFT), as known to the man skilled in the art of signal processing.

It can be noted that, the intensity/power of the ultrasound field generated by a given transducer will depend on the amplitude of the electric drive signal delivered by the generator system 10 at the operating frequency.

It must be noted here that a transducer will be considered to be not activated if, when fed with an electrical signal not having its operating frequency, it delivers an ultrasound field having an acoustic power output of less than 25% than the power/intensity it would deliver if fed with an electrical signal having the same acoustic power output at its operating frequency.

For a given implantable ultrasound generating device 12, a group of ultrasound generating transducers 20 may comprise a first ultrasound generating transducer or sub-group of transducers having at least a first operating frequency; and at least a second ultrasound generating transducer or sub-group of transducers having at least a second operating frequency which is not an operating frequency of the first ultrasound transducer or group of transducers. Thereby, if the group of transducers is fed, through the common electric connection circuit 24 with an electric signal having the second operating frequency and not the first operating frequency, only the second sub-group of transducers will be activated and will deliver a significant amount ultrasound power capable of having a measurable effect on the brain.

Preferably, in such a case, the first operating frequency is not an operating frequency of the second ultrasound transducer or group of transducers. Thus, if the group of transducers is fed, through the common electric connection circuit 24, with an electric signal having the first operating frequency and not the second operating frequency, only the first sub-group of transducers will be activated and will deliver ultrasound.

Thereby, it will be possible to activate either one or the other of the two sub-groups of transducers by feeding the group of transducers with an electric drive signal having the appropriate frequency content.

What is described above for two sub-groups of transducers can of course be applied to a higher number of sub-groups of transducers having each an exclusive operating frequency for the transducers of the sub-group. By feeding the group of transducers with an electric current having only one of the exclusive operating frequencies, only the corresponding sub-group of transducers will be activated.

For example, in the example of FIG. 1, it is suggested that the common holder 22 may comprise 7 transducers 20a, 20b, 20c, 20d, 20e, 20f, 20g each having a different operating frequency. In other words, each ultrasound generating transducer 20, which here belong to a same group of transducers, has an operating frequency different from any operating frequency of that group of transducers. In such a case, each transducer can be considered to be a sub-group of transducers. In such a case, each transducer can be activated individually. If the transducers are activated individually, there is no risk that the ultrasound field created by two transducers may superpose. Thus, there is no risk of uncontrolled creation of high intensity ultrasound field at any point of the treatment zone addressed by the implantable ultrasound generating device 12.

Figure 8:
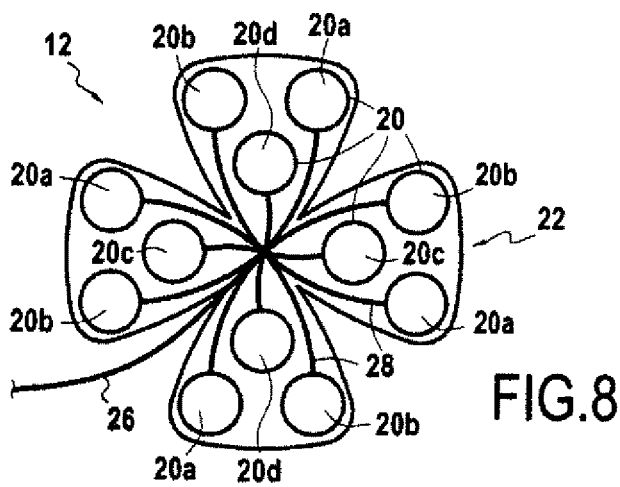

In the example of FIG. 8, it is suggested that the common holder 22 may comprise 4 different sub-groups of transducers 20a, 20b, 20c, 20d, each having a different operating frequency. In the shown example, the sub-groups 20a, 20b have each 4 transducers while the sub-groups 20c, 20d have each 2 transducers. Thus the sub-groups do not necessarily have the save number of transducers.

Figure 7:
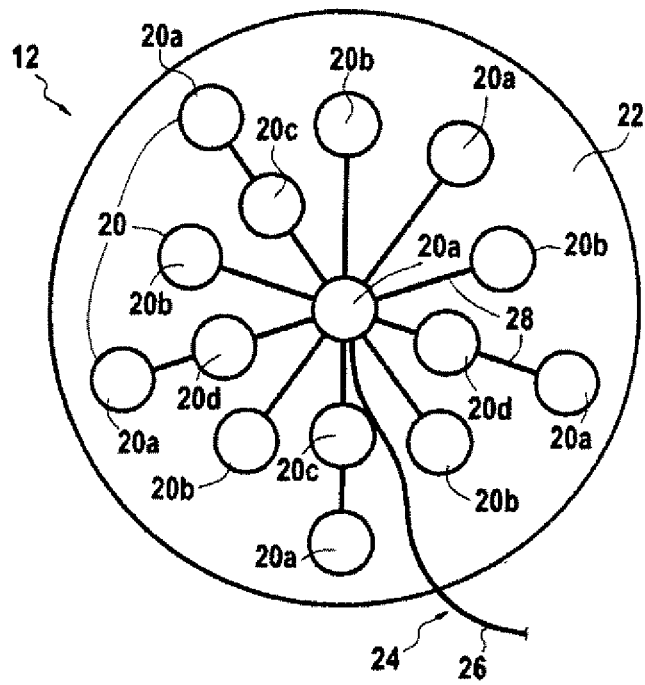
FIGS. 7 and 8 represent schematic top views of two further variants of a grid for a device according to the invention.
Figure 9:
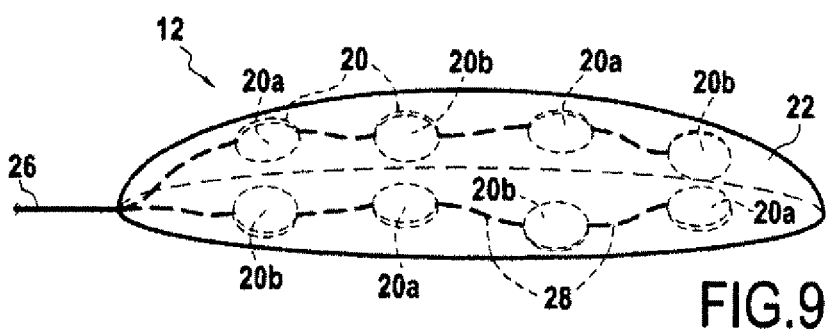
FIG. 9 represents a schematic side view of a further variant of a grid for a device according to the invention.

In the example of FIG. 9, it is suggested that the common holder 22 may comprise 2 different sub-groups of transducers 20a, 20b, each having 4 different transducers, thus having the same number of transducers in the different sub-groups. On FIGS. 6, 7 and 10 are shown other possible sub-groupings of transducers into sub-groups having different operating frequencies.

Preferably, on a given common holder 22, two transducers of a same subgroup are not adjacent in the sense that there is at least one transducer of another sub-group which is closer to the each of the two transducers of the same subgroup than a shortest distance between said two transducers of the same subgroup.

Indeed, it is of course interesting to have several ultrasound generating transducers in a same sub-group, thus several transducers having the same operating frequency, not the least because it allows making an implantable ultrasound generating device 12 having numerous transducers without the need to use too many different types of ultrasound generating transducers. However, in order to achieve a desired effect of reducing the risk of unwanted high ultrasound pressure spots in the treatment zone, which might otherwise result from the superposition of two ultrasound fields, it is preferable that two transducers of the same sub-group are not too close that their ultrasound emission zones intersect broadly in the treatment zone.

Indeed, an ultrasound generating transducer 20 can be considered to have a given ultrasound emission zone in the form approximately of a cone in which the intensity of the ultrasound field is significant. For example, in FIG. 2 is shown the case of said field of an implantable ultrasound generating device 12 having two sub-groups of two transducers: a first sub-group 20a1, 20a2, and a second sub-group 20b1, 20b2. The transducers 20a1, 20a2, belong to the same first sub-group and thus have a same first operating frequency. The transducers 20b1, 20b2, belong to the same second sub-group and thus have a same second operating frequency. Each transducer, when properly activated at its operating frequency, delivers an ultrasound field which can be characterized by a central emission axis Xa1, Xb1, Xa2, Xb2 and a border emission envelope Ea1, Eb1, Ea2, Eb2 which is shown here as a cone having the central emission axis as its axis of symmetry. The border emission envelope of the emission cone can be defined as the envelope containing all locations where the acoustic pressure of the ultrasound field is equal to at least a certain percentage, for example 25%, of the ultrasound field on the central axis at the same distance from the transducer. In real-world applications, the border envelope is not exactly a cone but, for the type of transducers used in the field of medical treatment ultrasound, can be considered as fairly close to a cone.

On FIG. 2 is shown that the emission cones of two adjacent transducers intersect. This is of course of interest to make sure that no zone of the brain is left untreated. However, in the intersection zone, there is a risk of superposition of the two fields created by the two adjacent transducers, if they would be activated simultaneously. On the other hand, in the example of FIG. 2, the emission cones of two non-adjacent transducers do not intersect in the treatment zone, or at least they may intersect at a distance along the central emission axis which is far enough from the transducers so that the acoustic pressure of each field in the intersection zone is greatly diminished, especially due to absorption by the brains tissues before reaching the intersection zone. For example, within a given implantable ultrasound generating device 12, transducers 20a1 and 20a2, or 20b1 and 20b2, belonging to the same sub-group, are chosen and arranged on the common holder such that, when the device is implanted in a patient's head, the emission cones of two transducers of a same sub-group do not intersect, or intersect at a distance from the respective transducers, along their central emission axis, where the ultrasound field pressure is less than or equal to the maximum acoustic pressure that would be generated if a single transducer was activated and had no interference from neighbouring transducers. Constructive interference is acceptable if the addition of the two ultrasound fields leads to a pressure value that is less than the maximum value of a single transducer, or is less than the maximum pressure value that is defined as "safe" for a given treatment.

Thus, in the example of FIG. 2, if the ultrasound generating device 12 is fed with an electric signal having only the first operating frequency, only the transducers 20a1 and 20a2 are activated, with no risk of superposition of the two fields in the treatment zone which may generate unsafe acoustic pressure levels. Similarly, if the ultrasound generating device 12 is fed with an electric signal having only the second operating frequency, only the transducers 20b1 and 20b2 are activated.

In some examples of an ultrasound generating device 12, the ultrasound generating transducers 20 may be connected to the common electrical connection circuit 24 through an implantable switch 50 which is connected, upstream, to the common electrical connection circuit 24 and, downstream, separately to several distinct sub-groups of one or several ultrasound generating transducers 20.

The implantable switch 50 forms part of the ultrasound generating device 12.

The implantable switch 50 selectively connects the common electrical connection circuit 24 to one of several distinct sub-groups of one or several ultrasound generating transducers 20, based on the electric drive signal which controls the implantable switch.

Figure 17:
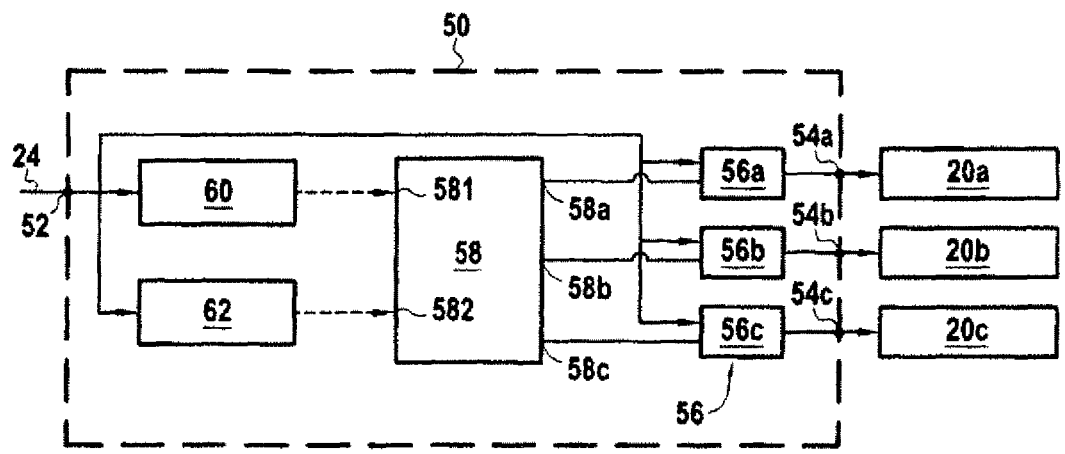
FIG. 17 represents schematically an implantable switch for an implantable ultrasound emitting grid and/or apparatus of the present invention.

An example of such implantable switch 50 is illustrated diagrammatically on FIG. 17.

The implantable switch 50 may comprise an input port 52 connected to the common electrical connection circuit 24, for example to the cable 26 of FIG. 1, for receiving the electric drive signal coming from the generator 10.

Figure 18:
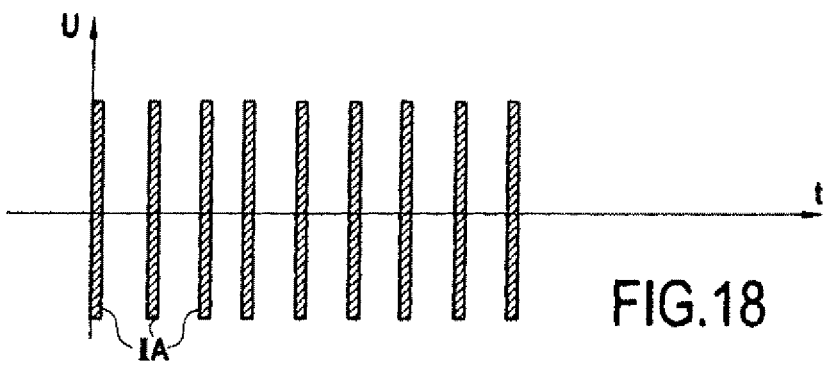
FIG. 18 represents schematically an example of an electric drive signal voltage.

The electric drive signal in the common electrical connection circuit 24 may be as shown diagrammatically on FIG. 18. The electric drive signal may comprise a series of signal bursts IA having a burst length for example between 1 and 100 milliseconds, preferably between 10 and 50 milliseconds. The signal bursts IA, herein called therapeutically active bursts IA, comprise at least an operating frequency of the transducers, for example within the frequency range of 500 kHz to 2 MHz, and have a power sufficient for activating the ultrasound generating transducers 20 so that they deliver therapeutically active ultrasounds.

The implantable switch 50 may comprise several output ports 54a, 54b, 54c which are each electrically connected separately to one of several distinct sub-groups of one or several ultrasound generating transducers 20. In the example of FIG. 18, only one ultrasound generating transducer 20a, 20b, 20c is associated to the corresponding output port 54a, 54b, 54c. With an implantable device 12 as shown on FIGS. 14 to 16, a given output port could be electrically connected to the three ultrasound generating transducers 20 arranged along a same row $D2_1$, $D2_2$, $D2_3$ along the second direction D2, such that the three ultrasound generating transducers 20 arranged along a same row would be driven simultaneously with the same drive signal to generate therapeutic ultrasounds.

The implantable switch 50 may comprise a relay stage 56 which may comprise, individually electrically connected to one of each output ports 54a, 54b, 54c, a respective individual relay 56a, 56b, 56c, which may be in the form of a solid state relay including transistors, thyristors, MOSFETs, etc. . . . . Each individual relay 56a, 56b, 56c, may comprise:
- a power input port connected to the common electrical connection circuit 24 to receive the electric drive signal;
- a power output port electrically connected to one of said several distinct sub-group of one or several ultrasound generating transducers, through a corresponding one of the output ports 54a, 54b, 54c;
- a gate port electrically connected to an output port of a switching stage.

In the embodiment of FIG. 17, the implantable switch 50 comprises a switching stage 58, which in this case comprises a number of output ports 58a, 58b, 58c, with one output port of the switching stage 58 associated to a gate port of a corresponding individual relay 56a, 56b, 56c of the relay stage 56. In the depicted embodiment, only one gate port of an individual relay 56a, 56b, 56c of the relay stage 56 is associated to one output port of the switching stage 58. For example, a solid state relay AQY277 from Panasonic Corporation can be used as a respective individual relay 56a, 56b, 56c.

In the depicted embodiment, the switching stage 58 has an energy input port 581 at which the switching stage 58 receives the energy necessary for its operation. The switching stage 58 also has a control port 582 which receives a clock signal according to which the switching stage 58 causes selective activation of the output ports 58a, 58b, 58c.

In the depicted embodiment the implantable switch 50 is energized from the electric drive signal.

Figure 19:
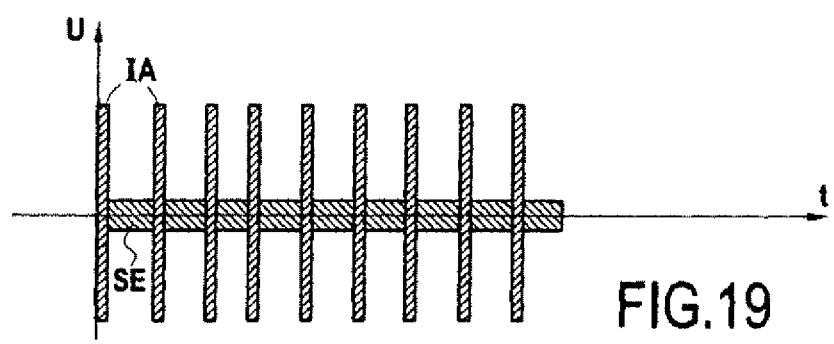
FIG. 19 represents schematically an example of an electric drive signal voltage comprising a switch energizing signal.

In some embodiments, the electric drive signal delivered by the generator 10 and carried by the common electrical circuit 24 may have a switch energizing portion, as depicted FIG. 19 on which it is seen that the electric drive signal comprises, between the therapeutically active bursts IA, a switch energizing signal SE. Preferably, the switch energizing signal SE does not comprise an operating frequency of the transducers. For example, the switch energizing signal SE may be offset of a resonant frequency of the transducers 20 by more than 10%, preferably by more than 20%.

If needed, a filter, such as a band-pass filter, may be provided between the switch input port 52 and the switching stage energy input port 581 so that only the switch energizing signal SE is fed to the energy input port 581.

If needed, a filter (not represented) may be provided between the switch input port 52 and a power input port of the relay stage 56 to filter out the switch energizing signal SE.

Figure 20:
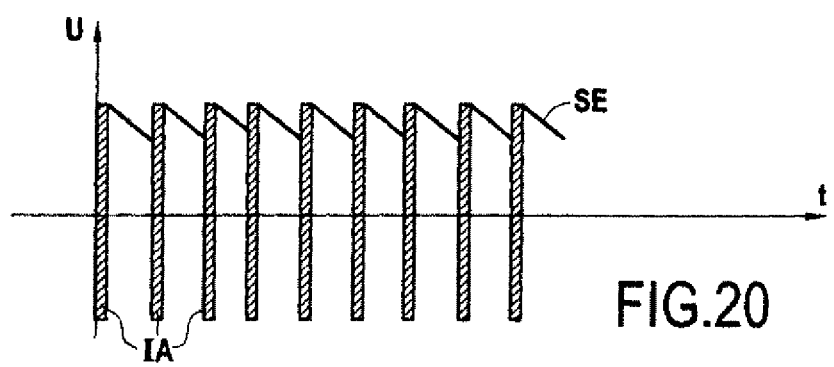
FIG. 20 represents schematically an example of a switch energizing signal voltage generated from an electric drive signal.

Preferably the implantable switch 50 generates a switch energizing signal SE from the electric drive signal, said switch energizing signal SE energizing the switch 50. For example, the implantable switch 50 may comprise a switch energizing signal generator 60 to generate a switch energizing signal SE from the electric drive signal. The switch energizing signal generator 60 may comprise for example a RC filter for filtering the electric drive signal. An example of a switch energizing signal SE generated by a switch energizing signal generator 60 is shown on FIG. 20. The switch energizing signal SE can for example comprise a low frequency signal, for example 50 Hz or 60 Hz signal. Alternatively, the switch energizing signal SE may comprise a signal having a frequency comprised between 200 KHz and 400 Khz.

Figure 21:
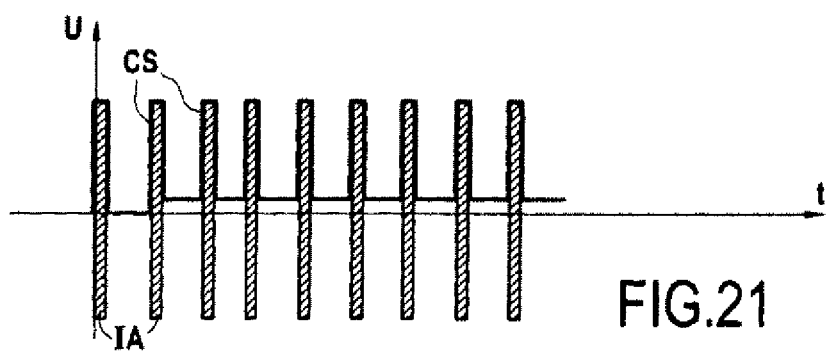
FIG. 21 represents schematically an example of a clock signal voltage generated from an electric drive signal.

The implantable switch 50 may generate a clock signal from the electric drive signal. Such a clock signal may be used by the switching stage 58 to cause the implantable switch to selectively connect the common electrical connection circuit 24, through the relay stage 56, to one at a time of said several distinct sub-groups of one or several ultrasound generating transducers 20. To that effect, the implantable switch 50 may comprise a clock signal generator 62 to generate a clock signal from the electric drive signal. For example, the clock signal generator may comprise a Schmitt trigger, which may be associated to an RC filter. The clock signal generator 62 may be located between the switch input port 52 and the switching stage control port 582. On FIG. 21 is illustrated an example of a clock signal CS which may be generated by a clock signal generator 62 based on the electric drive signal of FIG. 18. The clock signal CS may thus comprise a square binary signal having a raising edge and a falling edge. The raising edge may be triggered by the start of a therapeutically active burst IA. The falling edge may be triggered by the end of a therapeutically active burst IA. However, other relative configurations are possible between the therapeutically active burst IA and the clock signal CS.

The switching stage 58 of the implantable switch may comprise a digital counter which selectively activates, one at a time, one of several of its several outputs based on a clock signal. The digital counter may for example comprise a decade counter, for example of the industry standard generic 4017 integrated circuit type.

In the example of FIG. 17, the implantable switch 50 may connect, in a sequence, for example a predetermined sequence, the common electrical connection circuit 24 to one at a time of said several distinct sub-groups of one or several ultrasound generating transducers, based on the electric drive signal which controls the implantable switch.

An implantable switch 50 can alternatively comprise
- a high voltage analog switch, for example an HITACHI ECN3290,
- with a control stage comprising a micro-controller, also comprised within the implantable switch 50, to control the high voltage analog switch based on the electric drive signal.

In embodiments where the ultrasound generating treating device 12 comprises an implantable switch 50, as described above, the ultrasound generating transducers 20 of a given group may have the same resonant frequencies, even if pertaining to different sub-groups which are to be activated at different times.

In some embodiments, the implantable ultrasound generating treating device 12 may comprise phase difference inducing electrical components implemented in the power controller and/or the treating device. For a better compactness of the apparatus, and more specifically of its treating device, the phase difference inducing components may be integrated or associated to the ultrasound transducers. Such phase difference inducing components can for instance comprise filters, capacitors and combinations thereof.

In some embodiments, the implantable ultrasound generating device has, in front of one, some, or each of the ultrasound generating transducers, an ultrasound conditioning device, i.e. a device which affects the direction of propagation of the ultrasound waves generated by the transducer. Such device can include a refraction lens, e.g. a focusing or a defocusing lens, which affects the direction of propagation by refraction through non parallel surfaces of the device. Alternatively, or in combination, such device may affect the direction of propagation by diffraction of the ultrasound waves generated by the transducer.

In some embodiments, an ultrasound conditioning device may be formed as a portion of the holder material which covers a frontal surface of one, several or each of the ultrasound generating transducers. The frontal surface is the surface of the transducer which emits the ultrasound. It is turned towards the brain.

In the example of FIG. 11A is shown an example of a holder 22 made of a single sheet of material in which the ultrasound generating transducers are embedded. The holder thus exhibits a lower surface 38, turned towards the brain, and an upper surface 40 turned opposite the brain, towards the skull bone. In this example, the holder material exhibits, in front of some or each of the ultrasound generating transducers, a portion 42 of its lower surface 38, which is shaped convexly. As the transducers exhibit here a substantially flat frontal surface turned towards the brain, the interface of the material of the holder with the transducer exhibits a substantially flat surface, so that the portion 42 of the holder material which is in front of the ultrasound generating device can be assimilated to a plano-convex lens 42. Thus, the ultrasound wave, when propagating through the lower convex surface of the holder material, will be diffracted according to known laws of propagation, and the direction of propagation will be affected depending on the convexity of the lower surface of the ultrasound conditioning device formed as a portion 42 of the holder material, and depending on the difference in acoustic impedance between the holder material and the surrounding material at the interface with the holder.

In the example of FIG. 11B, is shown a variant where the holder material exhibits, in front of the ultrasound generating transducers, a portion 44 of its lower surface 38, which is shaped concavely. The portion of the holder material which is in front of the ultrasound generating device can be assimilated to a plano-concave lens 44. Such concave shaped lower surface portion may assist in achieving focalisation of ultrasound.

Alternatively, or in combination, the ultrasound emitting grid may include, in front of one, some or all the ultrasound generating transducers, one or several diffracting array(s) to cause diffraction of the ultrasound generated by the ultrasound generating transducers.

The diffraction array may be formed by the material of the holder, which may exhibit properties such as to cause diffraction of the ultrasound generated by the ultrasound generating transducers. For example, the material may include a diffracting array. Such array may include microbubbles of air or any suitable gas, or particles, or an array of ultrasound opaque inclusions which cause diffraction of the ultrasound wave, thus affecting its propagation direction.

The ultrasound emitting grid may include one or several ultrasound conditioning device(s), such as a refracting lens or a diffracting array distinct from said holder. In such a case, the ultrasound conditioning device(s) may be attached to the holder 22.

Use of ultrasound conditioning devices as above may allow to design an ultrasound generating grid which avoids unwanted superposition of the various waves generated by each ultrasound, for example for avoiding peak ultrasound power at certain locations of the treatment zone. Use of ultrasound conditioning devices as above may allow to design an ultrasound generating grid with more homogeneous distribution of the ultrasound power in the total volume of treatment zone.

In the case of a holder made of several sheets of material, the ultrasound conditioning device, when included in the material forming the holder, may be included in only one of the sheets. Such sheet may be the lowest sheet of material, having the lower surface 38. Alternatively, especially in the case of convex or concave shaped ultrasound conditioning devices, they may be included in a sheet intermediate between the transducers 20 and the lowest sheet of material, which thus may be of complementary shape and may exhibit a flat lower surface.

In the shown embodiment, the electrical connection network comprises a connection receiver 16 having a rigid casing. In this particular case, the rigid casing of the connection receiver is adapted to be fitted in a burr-hole performed in the skull of the patient to be treated. The casing may be of cylindrical shape, preferably of circular cylindrical shape. Said casing may comprises an upper wall 30 and a lower wall 32 connected by a circular peripheral wall 34.

The rigid casing may have an upper flange 36 of larger diameter than a lower portion of the casing. The lower portion may be received in the burr-hole while the upper flange may then rest on the upper external surface of the skull bone. The rigid casing of the connection receiver 16 may be fastened to the skull 1 by any suitable means, such as bone screws. The upper flange may be replaced by one or several peripheral tabs, possibly with hole(s) for receiving bone screws to attach the implantable connection receiver 16 to the skull. In a variant, the casing may comprise a peripheral external screwing thread formed on the external surface of the peripheral wall of the casing. In that embodiment, the connection receiver can advantageously be screwed manually in the burr-hole 3 of corresponding diameter by a surgeon.

For example, one or several connecting plugs may be located within the implantable rigid casing and may be adapted to physically connect with one or several connecting needle(s) 14 from the generator systems. A connecting needle 14 is preferably a transdermal needle. Such needles are suitable for piercing the patient's skin and the upper wall 30 of the implantable casing of the connection receiver before plugging into the connecting plugs inside the implantable casing. The upper wall 30 of the casing can be advantageously made of, or comprise a portion made of, an isolating concealable material like Silastic®, from the silicone manufacturer Dow Corning. This material can easily and automatically reseal when the needle 14 is withdrawn from the implantable connection receiver 16. Thus, the upper wall 30 forms an automatically re-sealable sealing gasket between the inside of the casing and the biological fluids and tissues of the patient's head. Advantageously, the transdermal needle 14 may be coated with an isolating material, for instance wax or plastic on its entire length except at its tip so that an electric contact can be established at its tip with a connecting plug inside the connection receiver to transfer electric current to the implantable connection receiver 16 without causing burning of the patient's skin. The embodiment of the invention represented in FIG. 1 depicts a two-way connection by means of a single transdermal needle 16 which carries, on one way, the electric drive signal and, on the other way, the ground connection between the generator system 10 and the implantable treating device 12, which in this case, has only one independent electric connection circuit 24, thus only one group of transducers. Two single-way needles could have been provided, one for the electric drive signal and one for the ground return.

However, in case of an implantable ultrasound generating device having several independent electrical connection circuits, an independent connection for each electrical signal corresponding to each independent electrical connection circuit would be needed, plus at least one common ground connection. This could be achieved with a single needle having one way per electrical signal plus one way for the ground return, or with several needles.

The ultrasound generating transducers 20 are preferably chosen into the group formed by piezo-composite elements, piezo-ceramic elements, CMUT elements (Capacitive micro-machined ultrasonic transducers), or PVDF elements (Poly(vinylidene fluoride)). Piezo-composite elements or piezo-ceramic elements usually have a size in the range of 1 to 50 mm in diameter. CMUT elements usually have a size in the range of 10 to 50 µm in diameter. Piezoelectric components are commonly used in the medical field as ultrasound transducers. A given transducer can comprise one or several discrete elements which are activated simultaneously. The transducers 20 may be held on the holder 22 by any suitable means. They can be held by being partially embedded or encapsulated in the material forming the holder 22. They can be held on the holder 22 by gluing, by riveting, or by stitching.

In embodiments where the implantable ultrasound generating device 12 comprises an implantable switch 50, the switch can advantageously be mounted on the holder 22, or, less preferably, in the connection receiver 16.

The generator system 10 is adapted for delivering electric drive signals to be delivered to the ultrasound generating transducers 20 of an associated ultrasound generating device 12. The generator system typically comprises an alternating voltage generator able to generate an electric signal at different frequencies. It shall be able to at least deliver alternating voltages at each of the operating frequencies of the associated ultrasound generating device 12. The generator delivers for example a sinusoidal electric voltage signal. Preferably, the generator shall be able to deliver an electric voltage being a combination of signals having at least two of said operating frequencies.

One example of a generator system that can be used with the inventive device may include a system that integrates signal generation, amplification, and control into a single unit. However, a generator system can also comprise one or several individual components performing one or more of these functions. For example, the generator can include an HP/Agilent 33120 function generator. If needed, it can also include for example one or more of an ENI 240L Broadband RF amplifier, of a Rhode and Schwarz RF power meter, and/or external computer controlling equipment over GPIB/Serial/USB interfaces. A computer interface, for example a touchscreen interface, can be provided to control the system and give the user feedback. A radiofrequency board that generates the RF signal and amplifies it may be provided, as well as a coupler to measure the delivered RF power, and matching components to tune the generator output to the impedance of the ultrasound elements. Preferably, the generator may be of a type capable to deliver 25-100 W peak RF power, capable of sending burst lengths with durations of 1 microsecond to continuous mode, and capable of sending bursts within the frequency range of 500 kHz to 2 MHz, preferably also capable to deliver bursts within the frequency range of 20 kHz to 200 MHz. Such a system can be controlled to send pulses with variable frequency and duty cycles for durations of approximately 2-5 minutes. The generator may be a class A/B RF system, which means that it is capable of generating nearly pure sinusoidal signals, but this may make the system rather large. In some embodiments, especially in the case where the generator is implantable, the generator could be a class D system, which tends to generate signals that are square wave on the output.

The operating frequencies of the ultrasound generating transducers 20 can range for example from 1 kHz to 100 MHz, Preferably, between 100 kHz and 10 MHz, more preferably between 500 KHz and 2 MHz. For example, in the case of an ultrasound generating device 12 having three sub-groups of ultrasound transducers, the respective sub-groups may have, as operating frequency, respectively 900 KHz, 1 MHz and 1.1 MHz.

The ultrasound generating transducers 20 of the implantable ultrasound generating device 12 of the invention can be planar or can be curved.

In addition to the ultrasound generating transducers 20, the holder 22 may advantageously hold at least one detection ultrasound transducer designed for echo-monitoring of the brain 3. Said detection transducer may thus be connected to the generator system to work at a different frequency from the ultrasound generating transducers 20 and to produce echo-monitoring onto a monitor implemented in or connected to the generator system. Alternatively, the detection ultrasound transducer(s) may operate as or "passive monitoring" where the transducer simply listens to the signals emitted by bubbles in the field. It is therefore possible with the apparatus of the invention to treat a brain disorder by ultrasound emission while in the same time echo-detect the area of the brain being treated. Such feed-back information permits to ensure clinicians of the microbubbles presence in the vessels and permits a monitoring of cavitation within the brain, with a safety closed loop feedback on the generator.

Preferably, the implantable ultrasound generating treating device 12 is made of non-ferromagnetic materials, preferably MRI compatible materials.

The holder 22 of the implantable ultrasound generating treatment device 12 extends preferably over a surface of extension exceeding 5 $cm^2$, preferably exceeding 25 $cm^2$. In some embodiments, the holder 22 may reach a surface of extension exceeding 100 $cm^2$, including a holder having a dimensions of up to 10×15 cm. The volume of the part of the brain which may treated, i.e. the treatment zone, by a single implantable ultrasound generating treatment device 12 according to the invention can reach up to 500 $cm^3$.

With such dimensions a much larger treatment zone of the brain may be treated with the apparatus according to the invention. Advantageously a substantial portion, or the entirety, of the cerebral hemisphere may be treated with such apparatus.

The holder may exhibit for example 1 to 4 transducers per square centimetre.

In the shown embodiments, directed to flexible holders, the transducers 20 are arranged on the holder 22 with a spacing between two transducers which have a size comparable to the size of the transducer, for example between 0.5 and 1.5 times the biggest dimension of the transducer in the plane of extension of the holder 22. However, transducers could be more closely arranged thanks to the selective activation of the transducers according to the invention.

Thus, the treatment zone can be much larger than that with other implantable devices, while still being selectable by proper choice of the size and positioning of the holder(s), and still being able to avoid skull bone absorption of the ultrasound waves. Indeed a given treatment apparatus can be provided with a set of different implantable ultrasound generating devices, such devices being for example different by their holder size, their holder shape (contour periphery, spatial configuration), their holder elastic or conformable properties, the type of transducers, the number of transducers, and/or the density of transducers, etc. . . . . . Indeed, designing and constructing of such various holders can be done at minimal cost.

It can be noted that an implantable ultrasound generating treatment device 12 according to the invention could comprise several independent holders. Preferably, in such a case, the different holders are connected to a single connection receiver 16 by a suitably designed electrical connection circuit. Such circuit may thus comprise several cables, for example with one cable per holder and each cable connecting the corresponding holder directly to the connection receiver. In a different configuration, the electric connection circuit could comprise an electrical cable between two holders, one holder being thus powered through the other holder.

The apparatus 1 of the invention, as described herein, is aimed at providing a solution for treating brain disorders, particularly brain tumours or neurodegenerative diseases such as Alzheimer's Disease, in complement to regular craniotomies. The apparatus 1 of the invention provides for emission of ultrasound waves, directly in the area of the brain affected.

Thanks to the flexibility of the implantable ultrasound generating device 12 according to the above described embodiment, it can advantageously be introduced underneath the skull bone through a burr-hole or a small craniotomy of a smaller dimension than the dimension of the holder. The flexible holder 22 may indeed be flexed and therefore folded to be slid through the burr-hole. However, the implantable ultrasound generating device 12 can also be implanted through a larger opening. For example, it can be implanted on the inner surface of a bone skull flap, with or without the dura-mater in place. If a portion of the dura-mater is removed, the flexible holder can replace at last part of the missing portion. In both cases, flexibility of the holder 22 will predominantly help in adapting the spatial configuration of the folder to that of the skull and/or the brain at the location of implantation, thereby minimizing adverse consequences of the presence of such a device inside the skull.

In one embodiment, the generator system is implanted in the patient's chest to have a totally implantable apparatus, In such a case, connection between the generator system and the implantable ultrasound emitting grid can be achieved by a mere electric cable, without need of a connection receiver or transdermic needles. Control of the generator is performed remotely by the clinician, for example, by radiofrequency or ultrasound.

The invention therefore proposes also a method for treatment of such brain disorders.

The method of the invention essentially consists in positioning, for example at the end of a traditional neurosurgical procedure (craniotomy debulking or keyhole biopsy), at least one implantable ultrasound generating device 12 of the apparatus previously described through a burr hole 3 or other opening in a patient's skull 1, before the skin closure of the patient. Alternatively, it can also be carried out without previous neurosurgical procedure. In that case, one or several burr holes 3 are drilled directly in the patient's skull 1 with the aim of implanting the implantable ultrasound generating device 12 of the apparatus of the invention. The positioning of the burr hole(s) 3 to drill in the skull may then be preferably determined prior to drilling, e.g. by neuro-navigational systems.

Once the implantable ultrasound generating device 12 has been implanted through a burr hole 3, the connection receiver 16 may be installed in said burr-hole 3. The connection receiver 16 can be secured to the skull 1 on its edges, for example by bone screws 5.

The cranial skin is then sutured over the implantable ultrasound generating device 12 and is preferably allowed to heal before any further action.

When the skin in the patient's head has healed, treatment of brain disorders can then be carried out. To that aim, the implantable ultrasound generating device 12 is connected to its generator system 10 by means of transdermal needle 14 implanted through the head's skin and into the connection receiver 16. The implantable ultrasound generating device 12 is then activated through control of the generator system 10 of the apparatus, which the surgeon or practitioner carrying out the treatment has previously set to specific treatment parameters.

When supplying power to said implantable ultrasound generating treating device 12, the generator is thus, for some embodiments, controlled for generating an electric drive signal comprising selectively, during an individual activation time, at least one or the other of:
- a first drive signal component having the first operating frequency; and of
- a second drive signal component having the second operating frequency; in order to drive exclusively either one or the other of:
- the first transducer or sub-group of transducers; and of
- the second transducer or sub-group of transducers.

Preferably, the two sub-steps will be conducted one after the other.

In the general case of several different sub-groups of transducers, the method will preferably provide that each sub-group of transducers 20 will be activated, each in turn, during one cycle, by generating, in turn, a corresponding electric drive signal comprising one operating frequency corresponding to one sub-group, and preferably not comprising the other operating frequencies corresponding the other sub-groups, except if two sub-groups can be activated simultaneously without any risk. If two sub-groups are to be activated at the same time, an electric drive signal comprising two operating frequencies is to be delivered through the same electrical connection circuit 24 during a joint activation time.

The electric drive signal having at least operation frequency will cause the activation of at least one sub-group during an individual activation time IA, after which another sub-group is activated during another individual activation time. An optional individual lapse time IL can be provided between two individual activation times IA, during which no sub-group of transducer is activated.

At the end of one cycle time C, each sub-group of transducers will have been activated. At the end of one cycle time C, a new similar cycle may be repeated. A cycle lapse time CL may be provided between two cycles, during which no sub-group of transducer is activated. Such cycle lapse time could be typically in the order of 1 s, for example comprised between 200 ms and 5 s.

The cycles may be repeated during a treatment time. Each transducer is for example activated for an individual activation time of 1 microsecond to 100 milliseconds during each activation IA. The delay between the initial activation of a single transducer and the subsequent activation is such that the net duty cycle (ON time divided by ON time plus OFF time) is typically less than 20% preferably less than 10% to avoid heating of tissues in the case of use for BBB disruption.

Figure 12A:
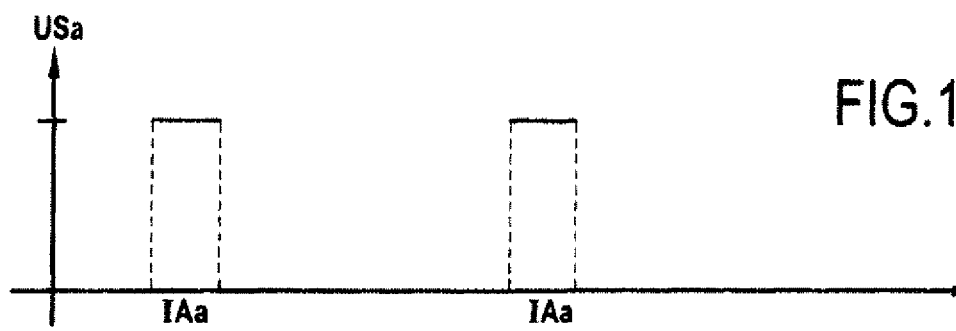
FIGS. 12A-D are time charts showing sequential activation of different transducers or sub-groups of transducers.
Figure 12B:
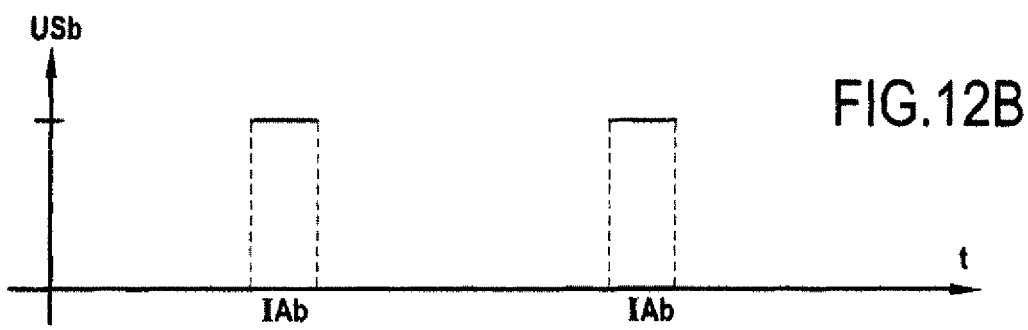
Figure 12C:
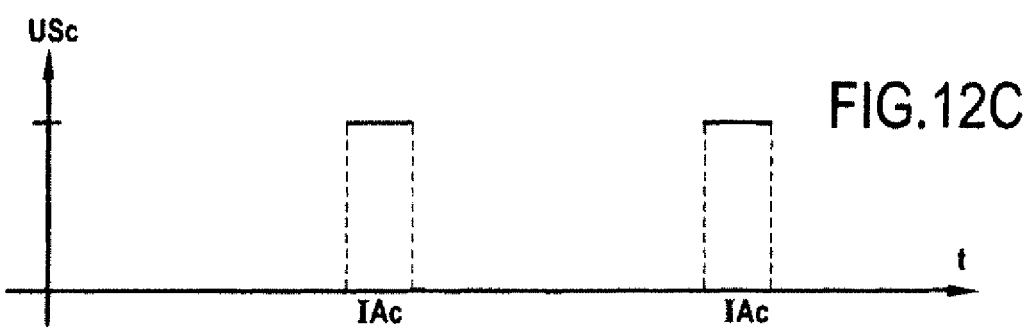
Figure 12D:
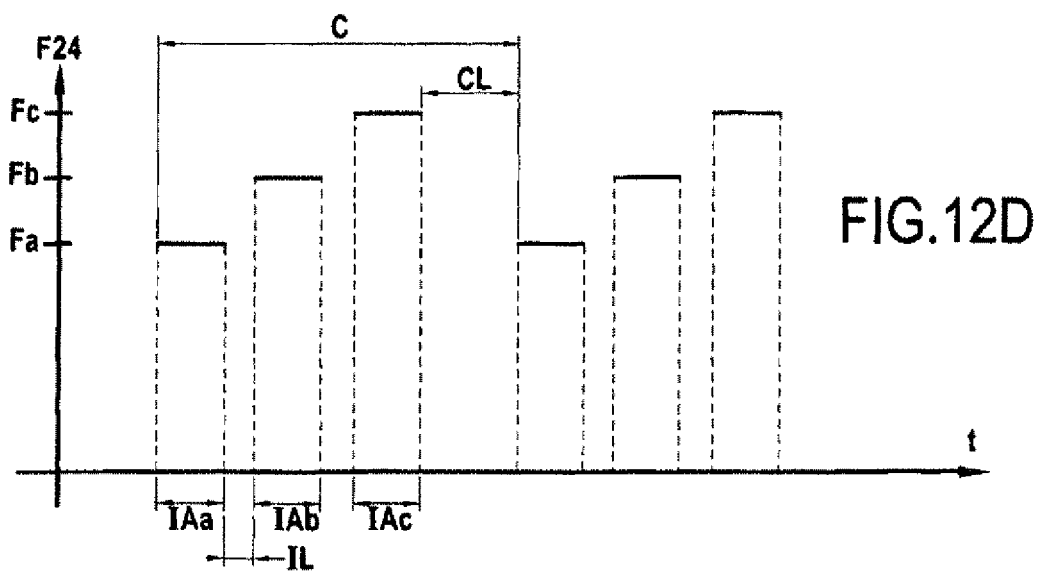

FIGS. 12A to 12D illustrate one example of a method according to the invention when using an implantable device having three sub-groups of transducers 20a, 20b and 20c, each having a different operating frequency Fa, Fb and Fc. FIG. 12D illustrates, as a function of time, the frequency F24 of an electric drive signal delivered by the generator to the implantable device 12 through the common electrical connection circuit 24. FIGS. 12A, 12B and 12 C illustrate respectively, as a function of time, an image of the ultrasound field intensity USa, USb, USc delivered respectively by the first, second and third sub-groups of transducers 20a, 20b and 20c.

As can be seen, the frequency F24 of an electric drive signal delivered by the generator successively takes a value Fa during an individual activation time IAa, thus activating exclusively the first sub-group of transducers 20a, a value Fb during an individual activation time IAb, thus activating exclusively the second sub-group of transducers 20b, and a value Fc during an individual activation time IAc, thus activating exclusively a third sub-group of transducers 20c. After a cycle lapse time CL, which may be optional, a new cycle is repeated.

In embodiments where the ultrasound generating treating device 12 comprises an implantable switch 50, as described above, the frequency of an electric drive signal delivered by the generator successively could the same value F during individual activation times IAa, IAb, IAc, while still activating exclusively a first sub-group of transducers 20, then subsequently exclusively a second sub-group of transducers 20, and subsequently exclusively a third sub-group of transducers 20.

It can be noted that, in addition to the control for the electrical signal frequency which includes setting the different individual activation, individual lapse and cycle lapse times, the treatment parameters may include the ultrasound amplitude, their duration, their possible pulsing, individual transducer control or parallel control, etc. . . . . Once the implantable ultrasound generating device 12 has been activated, physical waves are thus emitted in the patient's brain 2 to treat the brain area located beneath the implantable generator 4 in the patient's skull.

Emission of the physical waves in the brain to complete treatment lasts a predetermined treatment time. Once treatment is finished, the practitioner may unplug the transdermal needle 14 from the connection receiver 16 and the patient's head.

Such ultrasound emission in the brain, and specifically in the area of the brain that may have been surgically treated by the surgeon, for example by removal of tumorous tissue, is not absorbed by the skull since the transducers are positioned below the skull 1 itself.

According to a preferred method, the treatment with ultrasound may be used to enhance penetration and efficiency of selected drugs by increasing the permeability of the blood brain barrier, this increase in the permeability being induced by the ultrasound. Therefore, a method according to the invention may include the step of intravenously injecting a drug in the blood of a patient before or during ultrasound emission in the brain, said drug comprising therapeutic agents.

Moreover, the method may comprise a step of injecting in the patient's blood at least one contrast agent (Ultrasound sensitive micro-bubbles, ultrasound sensitive drugs, thermal sensitive drugs, nanoparticles, . . . ) prior to or during the emission of ultrasound with the treating device of the apparatus. The injection of such contrast agent advantageously helps and promotes opening of the blood brain barrier of the brain and enhances diffusion of the drugs within the brain tissues.

Moreover, the therapeutic agents of the drug may be coated with ultrasound sensitive release/carrier agents. In that way, the active drug is only released in the organism, and precisely only where the brain disorder to be treated is located when ultrasound waves emitted by the implantable ultrasound generating device 12 into the brain reach the coated therapeutic agents which have diffused in the patient's blood. By this mean, the active drug is only released in the selected region and doesn't affect the rest of the organism.

The apparatus and method of the invention advantageously allow monitoring, for example by means of the generator system 10 or by an external controller such as a computer, of the generation of ultrasound and, potentially, of the injection of contrast agent(s) and/or drug(s) into the patient's blood. A combined treatment sequence including injections of a contrast agent A and chemotherapeutic drug B together with ultrasound emission to open the blood brain barrier and enhance drug diffusion in the area of the brain to treat can be monitored.

Moreover, the apparatus and method of the invention, relying on ultrasound emission, can also be applied for other medical application than tumour and cancer treatment such as Alzheimer disease, psychiatric disorders, . . . . It can further be applied to induce a loco regional release of ultrasound sensible release/carrier agents such as nanoparticles, or liposomes for example.

Still preferably, if the drug injected in the patient's body is MRI-visible, its release within the brain can advantageously be monitored by MRI during or after the ultrasound emission treatment according to the method of the invention after connection of the implantable ultrasound generating device 12 of the apparatus of the invention to its generator system 10. Such MRI monitoring is possible in case the apparatus doesn't contain ferromagnetic material and the transdermal needles 19 used as connecting mains are coated with an isolating material. It allows controlling distribution of the effect of the ultrasound treatment over the treatment zone.

A flexible implantable device as described above may be inserted under the skull, between the skull bone and the meninges and may be made large to address a large zone of the brain. It allows treatment with therapeutic effect of diffuse brain tumors or other diffuse brain disorders. Moreover, an implantable device according to the invention may be used to deliver unfocused therapeutic ultrasound.

By activating only a selected number of ultrasound transducers at a time, an implantable device as described above allows avoiding undesired peak ultrasound pressure zones which could harm the tissues. Selective activation of the transducer, either individually or by sub-groups, minimizes the risk of undesired adverse consequences.

The invention claimed is:

1. Apparatus for the treatment of brain disorders, comprising:
   an implantable ultrasound generating treating device to induce brain disorder treatment by emission of ultrasound waves, wherein the implantable ultrasound generating treating device is implanted in or under a skull bone of a patient, wherein the implantable ultrasound generating treating device comprises an ultrasound emitting grid having several ultrasound generating transducers held by a common holder extending along a surface of extension, wherein the implantable ultrasound generating device comprises at least one group of several ultrasound generating transducers which are connectable by a common electrical connection circuit to a generator delivering electric drive signals driving the generation of ultrasound from the transducers, wherein the ultrasound generating transducers each have one or several operating frequencies,
   a generator to supply electricity to the implantable ultrasound generating treating device, wherein the ultrasound generating transducers within the group of transducers are connected to the common electrical connection circuit through an implanted switch which is connected, upstream, to the common electrical connection circuit and, downstream, separately to several distinct sub-groups of one or several ultrasound generating transducers, wherein the group of transducers consists of several transducers which are commonly driven by a same electrical drive signal, and wherein the electric drive signal serves both as power signal and as a control signal for operating selectively at least one or the other of a first transducer or sub-group of transducers within said group of transducers, and of a second transducer or sub-group of transducers within said group of transducers, wherein the switch is mounted on the holder, and further wherein an electrical connection network comprises a connection receiver having a rigid casing, a plug being located within the casing, the casing being distinct from the common holder and having an upper flange of larger diameter than a lower portion of the casing, wherein the implantable switch comprises a clock signal generator to generate a clock signal from the electric drive signal.

2. The apparatus according to claim 1, the clock signal causing the switch to selectively connect in a sequence the common electrical connection circuit to one at a time of said several distinct sub-groups of one or several ultrasound generating transducers.

3. The apparatus according to claim 1, wherein the implanted switch generates a switch energizing signal from the electric drive signal, said switch energizing signal energizing the switch.

4. The apparatus according to claim 1, wherein the electric drive signal comprises a switch energizing signal between therapeutically active bursts.

5. The apparatus according to claim 3, wherein the switch energizing signal does not comprise an operating frequency of the ultrasound generating transducers.

6. The apparatus according to claim 1, wherein the implanted comprises:
   a digital counter having a control port and a set of output ports, where the control port receives a clock signal generated from the electric drive signal;
   a series of relays having each:
   a power input port connected to the common electrical connection circuit to receive the electric drive signal;
   a power output port electrically connected to one of said several distinct sub-group of one or several ultrasound generating transducers;
   a gate port electrically connected to an output port of the digital counter.

7. The apparatus according to claim 1, wherein:
   the generator comprises a connector to electrically connect the generator and the implantable ultrasound generating treating device,
   the electrical connection circuit of the implantable ultrasound generating treating device comprises a connection receiver designed for cooperation with the connector of the generator to achieve electrical connection between the generator and the ultrasound generating treating device, and
   the connector of the generator comprises one or several transdermal needles suitable for plugging into the connection receiver through the patient's skin.

8. The apparatus according to claim 7, wherein the group of transducers consists of several transducers which are commonly driven by the same electrical drive signal and the electric drive signal serves both as power signal and as a control signal for operating selectively at least one or the other of a first transducer or sub-group of transducers within said group of transducers, and of a second transducer or sub-group of transducers within said group of transducers, and characterized in that the generator comprises only one two-way transdermal needle or only two one-way transdermal needles for operating selectively at least one or the other of a first ultrasound generating transducer or sub-group of ultrasound generating transducers, and of a second ultrasound generating transducer or sub-group of ultrasound generating transducers of a same group of transducers.

9. A method for treating brain disorders with an apparatus according to claim 1, comprising steps of:
   performing at least one opening into the skull of a patient,
   implanting through said opening an implantable ultrasound generating treating device,
   surgically closing a skin,
   connecting the implantable ultrasound generating treating device to a generator system,
   activating the generator system for supplying power to said implantable ultrasound generating treating device and thereby inducing ultrasound wave emission into the brain,
   treating an area of the brain located beneath the implantable ultrasound generating treating device by ultrasound waves emission into the brain during a determined period, and
   deactivating the generator system when treatment is complete, wherein the step of supplying power to said implantable ultrasound generating treating device includes:
   a step of generating the electric drive signal;
   selectively connecting the common electrical connection circuit through the implanted switch to one at a time of said several distinct sub-groups of one or several ultrasound generating transducers.

10. A method for treating brain disorders according to claim 9, comprising connecting in a sequence the common electrical connection circuit one at a time of said several distinct sub-groups of one or several ultrasound generating transducers.

11. A method for treating brain disorders according to claim 10, comprising connecting in a predetermined sequence the common electrical connection circuit one at a time of said several distinct sub-groups of one or several ultrasound generating transducers.

12. Apparatus for the treatment of brain disorders, comprising:
an implantable ultrasound generating treating device to induce brain disorder treatment by emission of ultrasound waves, wherein the implantable ultrasound generating treating device is implanted in or under skull bone of a patient, wherein the implantable ultrasound generating treating device comprises an ultrasound emitting grid having several ultrasound generating transducers held by a common holder extending along a surface of extension, wherein the implantable ultrasound generating device comprises at least one group of several ultrasound generating transducers which are connectable by a common electrical connection circuit to a generator delivering electric drive signals driving the generation of ultrasound from the transducers, wherein the ultrasound generating transducers each have one or several operating frequencies,
a generator to supply electricity to the implantable ultrasound generating treating device, wherein the ultrasound generating transducers within the group of transducers are connected to the common electrical connection circuit through an implanted switch which is connected, upstream, to the common electrical connection circuit and, downstream, separately to several distinct sub-groups of one or several ultrasound generating transducers, wherein the group of transducers consists of several transducers which are commonly driven by a same electrical drive signal, and wherein the electric drive signal serves both as power signal and as a control signal for operating selectively at least one or the other of a first transducer or sub-group of transducers within said group of transducers, and of a second transducer or sub-group of transducers within said group of transducers, wherein the switch is mounted on the holder, and further wherein an electrical connection network comprises a connection receiver having a rigid casing, a plug being located within the casing, the casing being distinct from the common holder and having an upper flange of larger diameter than a lower portion of the casing wherein the implanted switch comprises:
a digital counter having a control port and a set of output ports, where the control port receives a clock signal generated from the electric drive signal;
a series of relays having each:
a power input port connected to the common electrical connection circuit to receive the electric drive signal;
a power output port electrically connected to one of said several distinct sub-group of one or several ultrasound generating transducers;
a gate port electrically connected to an output port of the digital counter.

13. The apparatus according to claim 12, wherein the implanted switch generates a clock signal from the electric drive signal, said clock signal causing the switch to selectively connect in a sequence the common electrical connection circuit to one at a time of said several distinct sub-groups of one or several ultrasound generating transducers.

14. The apparatus according to claim 12, wherein the implanted switch generates a switch energizing signal from the electric drive signal, said switch energizing signal energizing the switch.

15. The apparatus according to claim 12, wherein the electric drive signal comprises a switch energizing signal between therapeutically active bursts.

16. The apparatus according to claim 15, wherein the switch energizing signal does not comprise an operating frequency of the ultrasound generating transducers.

17. The apparatus according to claim 14, wherein:
the generator comprises a connector to electrically connect the generator and the implantable ultrasound generating treating device,
the electrical connection circuit of the implantable ultrasound generating treating device comprises a connection receiver designed for cooperation with the connector of the generator to achieve electrical connection between the generator and the ultrasound generating treating device, and
the connector of the generator comprises one or several transdermal needles suitable for plugging into the connection receiver through the patient's skin.

18. The apparatus according to claim 14, wherein the group of transducers consists of several transducers which are commonly driven by the same electrical drive signal and the electric drive signal serves both as power signal and as a control signal for operating selectively at least one or the other of a first transducer or sub-group of transducers within said group of transducers, and of a second transducer or sub-group of transducers within said group of transducers, and characterized in that the generator comprises only one two-way transdermal needle or only two one-way transdermal needles for operating selectively at least one or the other of a first ultrasound generating transducer or sub-group of ultrasound generating transducers, and of a second ultrasound generating transducer or sub-group of ultrasound generating transducers of a same group of transducers.

19. A method for treating brain disorders with an apparatus according to claim 12, comprising steps of:
performing at least one opening into the skull of a patient, implanting through said opening an implantable ultrasound generating treating device,
surgically closing skin,
connecting the implantable ultrasound generating treating device to the generator system,
activating the generator system for supplying power to said implantable ultrasound generating treating device and thereby inducing ultrasound wave emission into the brain, —treating an area of the brain located beneath the implantable ultrasound generating treating device by ultrasound waves emission into the brain during a determined period, and—deactivating the generator system when treatment is complete, wherein the step of supplying power to said implantable ultrasound generating treating device includes:
a step of generating the electric drive signal;
selectively connecting the common electrical connection circuit through the implanted switch to one at a time of said several distinct sub-groups of one or several ultrasound generating transducers.

20. The method for treating brain disorders according to claim 19, comprising connecting in a sequence the common electrical connection circuit one at a time of said several distinct sub-groups of one or several ultrasound generating transducers.

21. A method for treating brain disorders according to claim 20, comprising connecting in a predetermined sequence the common electrical connection circuit one at a time of said several distinct sub-groups of one or several ultrasound generating transducers.

* * * * *